(12) United States Patent
Braddock et al.

(10) Patent No.: US 12,234,489 B2
(45) Date of Patent: Feb. 25, 2025

(54) COMPOSITIONS FOR TREATING ECTOPIC CALCIFICATION DISORDERS, AND METHODS USING SAME

(71) Applicant: YALE UNIVERSITY, New Haven, CT (US)

(72) Inventors: Demetrios Braddock, New Haven, CT (US); Enrique De La Cruz, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 18/068,256

(22) Filed: Dec. 19, 2022

(65) Prior Publication Data

US 2023/0227800 A1 Jul. 20, 2023

Related U.S. Application Data

(63) Continuation of application No. 17/075,398, filed on Oct. 20, 2020, now abandoned, which is a continuation of application No. 15/777,446, filed as application No. PCT/US2016/063034 on Nov. 21, 2016, now abandoned.

(60) Provisional application No. 62/257,883, filed on Nov. 20, 2015.

(51) Int. Cl.
| | |
|---|---|
| C12N 9/16 | (2006.01) |
| A61K 38/00 | (2006.01) |
| A61K 38/38 | (2006.01) |
| A61K 38/46 | (2006.01) |
| A61K 39/395 | (2006.01) |
| C07K 14/76 | (2006.01) |
| C12N 9/14 | (2006.01) |

(52) U.S. Cl.
CPC .............. *C12N 9/16* (2013.01); *A61K 38/385* (2013.01); *A61K 38/465* (2013.01); *A61K 39/395* (2013.01); *C07K 14/76* (2013.01); *C12N 9/14* (2013.01); *C12Y 301/03036* (2013.01); *C12Y 301/04001* (2013.01); *C12Y 301/04012* (2013.01); *C12Y 306/01009* (2013.01); *A61K 38/00* (2013.01); *C07K 2319/00* (2013.01); *C07K 2319/02* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 5,968,508 A | 10/1999 | Goldfine et al. |
| 6,043,056 A | 3/2000 | Yue et al. |
| 6,358,923 B1 | 3/2002 | Yue et al. |
| 7,323,542 B2 | 1/2008 | Balian et al. |
| 7,888,372 B2 | 2/2011 | Millan et al. |
| 8,846,603 B2 | 9/2014 | Quinn et al. |
| 9,744,219 B2 | 8/2017 | Braddock et al. |
| 9,913,881 B2 | 3/2018 | Braddock et al. |
| 10,064,917 B2 | 9/2018 | Braddock et al. |
| 10,213,483 B2 | 2/2019 | Otterlei et al. |
| 2007/0004913 A1 | 1/2007 | Challita-Eid et al. |
| 2007/0015145 A1 | 1/2007 | Woolf et al. |
| 2008/0273206 A1 | 11/2008 | Genge et al. |
| 2010/0203076 A1 | 8/2010 | Fotin-Mleczek et al. |
| 2014/0154774 A1 | 6/2014 | Quinn et al. |
| 2014/0349369 A1 | 11/2014 | Buechler et al. |
| 2014/0377859 A1 | 12/2014 | Quinn et al. |
| 2015/0024460 A1 | 1/2015 | Quinn et al. |
| 2018/0371434 A1 | 12/2018 | Braddock et al. |

FOREIGN PATENT DOCUMENTS

| | | |
|---|---|---|
| JP | 2008188015 A | 8/2008 |
| JP | 2018537093 A | 12/2018 |
| RU | 2013142583 A | 4/2015 |
| WO | 2006135925 A2 | 12/2006 |
| WO | 2008105911 A2 | 9/2008 |
| WO | 2011113027 A2 | 9/2011 |
| WO | 2012125182 A1 | 9/2012 |
| WO | 2014126965 A2 | 8/2014 |
| WO | 2016100803 A2 | 6/2016 |

OTHER PUBLICATIONS

Chen et al., "Fusion Protein Linkers: Property, Design and Functionality", Adv Drug Deliv Rev., 65 (10), pp. 1357-1369, Oct. 15, 2013 (Oct. 15, 2013).
Koike et al., "The N-terminal hydrophobic sequence of autotaxin (ENPP2) functions as a signal peptide", Genes to Cells, 11 (2), pp. 133-142, Jan. 4, 2006.
Borza et al., "Structure and function of the ecto-nucleotide pyrophosphatase/phosphodiesterase (ENPP) family: Tidying up diversity", J. Biol Chem., 298 (2), pp. 1-12, Dec. 24, 2021.
European Search Report for European Patent Application 16867323.4 issued Mar. 21, 2019.
European Supplemental Partial Search Report for European Patent Application No. 14751154.7 issued Nov. 7, 2016.
Extended European Search Report for European Patent Application No. 14751154.7 issued Feb. 16, 2017.
Extended European Search Report for European Patent Application No. 16797290.0 issued Jun. 25, 2019.
International Search Report and Written Opinion for PCT International Application No. PCT/US2016/063034 issued Apr. 20, 2017.
PCT International Search Report and Written Opinion for PCT International Application No. PCT/US2014/015945 Issued Jul. 30, 2014.
PCT International Search Report and Written Opinion for PCT International Application No. PCT/US2016/033236 Issued Oct. 27, 2016.

(Continued)

*Primary Examiner* — Suzanne M Noakes
(74) *Attorney, Agent, or Firm* — Saul Ewing LLP; Kathryn Doyle; Domingos J. Silva

(57) ABSTRACT

The present invention includes compositions and methods for treating disease and disorders associated with pathological calcification or pathological ossification.

13 Claims, 5 Drawing Sheets

Specification includes a Sequence Listing.

(56) References Cited

OTHER PUBLICATIONS

UniProt Accession No. O14638, ENPP3_HUMAN, Jan. 7, 2015 [online]. [Retrieved on Jan. 19, 2017]. Retrieved from the internet <URL: http://www.uniprot.org/uniprot/O14638.txt?version=133>.

Albright, et al., "ENPP1-Fc prevents mortality and vascular calcifications in rodent model of generalized arterial calcification of infancy", Nat Commun. 6, 2015, 10006.

Albright, et al., "Molecular basis of purinergic signal metabolism by ectonucleotide pyrophosphatase/phosphodiesterases 4 and 1 and implications in stroke", J Biol Chem. 289(6), 2014, 3294-3306.

Albright, et al., "NPP4 is a procoagulant enzyme on the surface of vascular endothelium", Blood. 120(22), 2012, 4432-4440.

Anonymous, "UPI000511D809", Retrieved from the Internet Mar. 7, 2019, <https://www.uniprot.org/uniparc/UPI000 511D809>, Oct. 2014.

Calvert, et al., "The Provisional Patent Application: What You Need to Know", Inventors Eye. United States Patent and Trademark Office <www.uspto.gov/ learning-and-resources/newsletter/inventors-eye/provisional-patent-application-what-you-need-know>, Apr. 2010, 5 pages.

Cimpean, et al., "Substrate-specifying determinants of the nucleotide pyrophosphatases/phosphodiesterases NPP1 and NPP2", Biochem J. 381(Pt 1), 2004, 71-77.

Döhler, et al., "Crystal structure and substrate binding mode of ectonucleotide phosphodiesterase/pyrophosphatase-3 (NPP3)", Sci Rep. 8(1), Jul. 2018, 10874.

Gijsbers, et al., "Functional characterization of the non-catalytic ectodomains of the nucleotide pyrophosphatase/ phosphodiesterase NPP1", Biochem J. 371(Pt 2), Apr. 15, 2003, 321-330.

Goding, et al., "Physiological and pathophysiological functions of the ecto-nucleotide pyrophosphatase/ phosphodiesterase family", Biochim Biophys Acta. 1638(1), 2003, 1-19.

Jansen, et al., "Proteolytic maturation and activation of autotaxin (NPP2), a secreted metastasis-enhancing ysophospholipase D", J Cell Sci. 118(Pt 14), 2005, 3081-3089.

Jansen, et al., "Structure of NPP1, an ectonucleotide pyrophosphatase/ phosphodiesterase involved in tissue calcification", Structure. 20(11), 2012, 1948-1959.

Jin-Hua, et al., "Molecular Coning and Chromosomal Localization of PD-Iβ (PDNP3), a New Member of the Human Phosphodiesterase I Genes", Genomics 45, 1997, 412-415.

Johnson, et al., "Differential mechanisms of inorganic pyrophosphate production by plasma cell membrane glycoprotein-1 and B10 in chondrocytes", Arthritis Rheum. 42(9), 1999, 1986-1997.

Johnson, et al., "Linked deficiencies in extracellular PP(i) and osteopontin mediate pathologic calcification associated with defective PC-1 and ANK expression", J Bone Miner Res. 18(6), 2003, 994-1004.

Johnson, et al., "The Nucleoside Triphosphate Pyrophosphohydrolase Isozyme PC-1 Directly Promotes Cartilage Calcification Through Chondrocyte Apoptosis and Increased Calcium Precipitation by Mineralizing Vesicles", The Journal of Rheumatology 28 (12), Dec. 2001, 2681-2691.

Lee, et al., "Cloning, chromosomal localization, and tissue expression of autotaxin from human teratocarcinoma cells", Biochem Biophys Res Commun. 218(3, 1996, 714-719.

Lieben, et al., "Normocalcemia is maintained in mice under conditions of calcium malabsorption by vitamin D-induced inhibition of bone mineralization", J Clin Invest. 122(5), 2012, 1803-1805.

Schetter, et al., "Nucleoporins NPP-1, NPP-3, NPP-4, NPP-11 and NPP-13 are required for proper spindle orientation in C. elegans", Dev Biol. 289(2), Jan. 15, 2006, 360-371.

Shankar, et al., "Progeria—A Brief Review", International Journal of Pharma and Bio Sciences 2, 2010, 1-14.

Stefan, et al., "NPP-type ectophosphodiesterases: unity in diversity.", Trends Biochem Sci. 30(10), Oct. 2005, 542-550.

Terkeltaub, "Physiologic and pathologic functions of the NPP nucleotide pyrophosphatase/phosphodiesterase family focusing on NPP1 in calcification.", Purinergic Signal. 2(2), Jun. 2, 2006, 371-377.

Tsai, et al., "The Ectoenzyme E-NPP3 Negatively Regulates ATP-Dependent Chronic Allergic Responses by Basophils and Mast Cells", Immunity 42, Feb. 2015, 279-293.

Whisstock, et al., "Prediction of proteinfunction fromprotein sequence and structure", Quarterly Reviews of Biophysics 36, 3 (2003), pp., 2003, 307-340.

Witkowski, et al., "Conversion of a Beta-Ketoacyl Synthase to a Malonyl Decarboxylase by Replacement of the Active-Site Cysteine With Glutamine", Biochemistry 38(36), Sep. 1999, 11643-11650.

Zhang, et al., "The interaction of cationic polymers and their bisphosphonate derivatives with hydroxyapatite", Macromol Biosci. 7(5), May 10, 2007, 656-670 (Abstract Only).

Buckley, et al., "Plasma cell membrane glycoprotein PC-1. cDNA cloning of the human molecule, amino acid sequence, and chromosomal location", J Biol Chem. 265(29), Oct. 1990, 17506-17511.

Robbie, et al. "A novel investigational Fc-modified humanized monoclonal antibody, motavizumab-YTE, has an extended half-life in healthy adults." Antimicrobial agents and chemotherapy 57.12 (2013): 6147-6153.

Okawa, et al., "Mutation in Npps in a mouse model of ossification of the posterior longitudinal ligament of the spine", Nat Genet. 19(3), Jul. 1998, 271-273.

Li, et al. "Serum phosphate concentration and incidence of stroke: a systemic review and meta-analysis." Neurological sciences 35.12 (2014): 1877-1882.

Nakanishi, et al. "Development and therapeutic application of transposon-based vectors." Yakugaku Zasshi: Journal of the Pharmaceutical Society of Japan 129.12 (2009): 1433-1443.

Mackenzie, et al. "New insights into NPP1 function: lessons from clinical and animal studies." Bone 51.5 (2012): 961-968.

Nitschke, Y et al. "Generalized arterial calcification of infancy and pseudoxanthoma elasticum can be caused by mutations in either ENPP1 or ABCC6." The American Journal of Human Genetics 90.1 (2012): 25-39.

Nitschke, et al. "Generalized arterial calcification of infancy and pseudoxanthoma elasticum: two sides of the same coin." Frontiers in genetics 3 (2012): 302.

Rutsch, et al. "Genetics in arterial calcification: pieces of a puzzle and cogs in a wheel." Circulation research 109.5 (2011): 578-592.

1  M.W. Markers
2  Partially Purified ENPP3
3  Starting Crude Material

COMPOSITIONS FOR TREATING ECTOPIC CALCIFICATION DISORDERS, AND METHODS USING SAME

CROSS-REFERENCE TO RELATED APPLICATIONS

This present application is a continuation of, and claims priority to, U.S. patent application Ser. No. 17/075,398, filed Oct. 20, 2020, which is a continuation of, and claims priority to, U.S. patent application Ser. No. 15/777,446, filed May 18, 2018, which is a 35 U.S.C. § 371 national phase application from, and claims priority to, International Application No. PCT/US2016/063034, filed Nov. 21, 2016, and published under PCT Article 21 (2) in English, which claims priority under 35 U.S.C. § 119 (e) to U.S. Provisional Application No. 62/257,883, filed Nov. 20, 2015, all of which are incorporated herein by reference in their entireties.

INCORPORATION-BY-REFERENCE OF MATERIAL SUBMITTED VIA THE OFFICE ELECTRONIC FILING SYSTEM

This disclosure contains one or more sequences in a computer readable format in an accompanying.xml file titled "047162-7077US3_Seq Listing.nrl" which is 46.2 KB in size and was created Dec. 19, 2022, the contents of which are incorporated herein by reference in their entirety.

BACKGROUND OF THE INVENTION

Calcification is the accumulation of calcium salts in a body tissue. It normally occurs during formation of bone, but calcium can also be deposited abnormally in soft tissues such as arteries, cartilage and heart valves. Vascular calcification frequently develops in patients with atherosclerosis, stroke, valvular disease and varicosis. Advanced age and metabolic disorders, including diabetes mellitus are contributing factors.

Ossification refers to the process of bone tissue formation or bone remodeling orchestrated by the osteoblasts. Ossification allows bones to form while a fetus is still in the womb, and also converts various types of connective tissue into bone. The two main processes of ossification are intra-membranous ossification and intra-cartilaginous ossification, which differ based on the area of the body in which the cartilage is located.

Abnormalities in the levels of calcification and ossification lead to a spectrum of diseases, a few examples of such as general arterial calcification of infancy (GACI), idiopathic infantile arterial calcification (IIAC), pseudoxanthoma elasticum (PXE), ossification of posterior longitudinal ligament (OPLL), medial wall vascular calcification (MWVC), autosomal recessive hypophosphatemia rickets type-2 (ARHR2), end state renal disease (ESRD), chronic kidney disease-bone/mineral disorder (CKD-MBD), X-linked hypophosphatemia (XLH), age related osteopenia, calcific uremic arteriolopathy (CUA) and hypophosphatemic rickets.

GACI is an ultra-rare neonatal disease characterized by infantile onset of widespread arterial calcifications in large and medium sized vessels, resulting in cardiovascular collapse and death in the neonatal period. The disease presents clinically with heart failure, respiratory distress, hypertension, cyanosis, and cardiomegaly. The prognosis is grave, with older reports of a mortality rate of 85% at six months, while recently intensive treatment with bisphosphonates (such as etridonate) has lowered mortality to 55% at six months. Tempering this apparent progress is the severe skeletal toxicity associated with prolonged use of etridonate in patients with GACI, and the ineffectiveness of bisphosphonates to prevent mortality in some patients even when instituted early. Further, the limited available data makes it difficult to determine if bisphosphonate treatment is truly protective or reflects the natural history of the disease in less effected patients. Interestingly, serum PPi levels appear to be significantly depleted in GACI patients.

Kidneys are integral to maintenance of normal bone and mineral metabolism, including excretion of phosphate. In 2003, 19.5 million U.S. adults have chronic kidney disease (CKD), and 13.6 million had stage 2-5 CKD, as defined by the National Kidney Foundation Kidney Disease Outcomes Quality Initiative (NKFK/DOQI). The prevalence of ESRD is increasing at an alarming rate. In 2000, end stage kidney disease developed in over 90,000 people in the U.S. The population of patients on dialysis therapy or needing transplantation was 380,000 in 2003, and became 651,000 patients in 2010. Care for patients with ESRD already consumes more than $18 billion per year in the U.S., a substantial burden for the health care system. Importantly, patients with kidney failure are unable to appropriately regulate serum mineral balance and tend to retain phosphate that is absorbed from the various dietary components. A high serum level of phosphate is associated with excessive secretion of parathyroid hormone and a tendency to calcification of the soft tissues, including blood vessels.

In patients with kidney failure, excess removal of phosphate and pyrophosphate anions can occur during hemodialysis or peritoneal dialysis. Depletion of these anions from tissues and plasma leads to disorders of bone and mineral metabolism, including osteomalacia and calcification of soft tissues and bone disease. Deposition of calcium into the small vessels of the skin causes an inflammatory vasculitis called calciphylaxis, which can lead to gangrene of the skin and underlying tissues, resulting in severe, chronic pain. Calciphylaxis may necessitate amputation of the affected limb and is commonly fatal, with no effective treatment for this condition. It is thus important to regulate the amount of pyrophosphate in the system and reduce the occurrence of calciphylaxis in patients.

CUA is a fatal disease seen in patients with CKD on dialysis. Calcification of small arteries leads to tissue/skin ischemia, infarction and thrombosis, with patient mortality close to 80%. Currently there are 450,000 patients on dialysis in the U.S. who are at risk of acquiring CUA, and there is no FDA approved treatments for the disease. CUA has hallmarks resembling GACI and other disorders of calcification, exhibiting low levels of PPi and high levels of fibroblast growth factor 23 (FGF23). In ESRD patients requiring dialysis, this calcification process is further accelerated, with an average life-expectancy of 5-6 years.

PXE is a heritable disorder characterized by mineralization of elastic fibers in skin, arteries and the retina, which results in dermal lesions with associated laxity and loss of elasticity, arterial insufficiency, cardiovascular disease and retinal hemorrhages leading to macular degeneration. Mutations associated with PXE are also located in the abcc6 gene. Characteristic skin lesions (yellowish papules and plaques and laxity with loss of elasticity, typically seen on the face, neck, axilla, antecubital fossa, popliteal fossa, groin and periumbilical areas) are generally an early sign of PXE and result from an accumulation of abnormal mineralized elastic fibers in the mid-dermis. They are usually detected during childhood or adolescence and progress slowly and often unpredictably. A PXE diagnosis can be confirmed by a skin biopsy that shows calcification of fragmented elastic fibers in the mid- and lower dermis. The skin manifestations are among the most common characteristics of PXE, but the ocular and cardiovascular symptoms are responsible for the morbidity of the disease.

Common cardiovascular complications of PXE are due to the presence of abnormal calcified elastic fibers in the internal elastic lamina of medium-sized arteries. The broad spectrum of phenotypes includes premature atherosclerotic changes, intimal fibroplasia causing angina or intermittent claudication or both, early myocardial infarction and hypertension. Fibrous thickening of the endocardium and atrioventricular valves can also result in restrictive cardiomyopathy. Approximately 10%, of PXE patients also develop gastrointestinal bleeding and central nervous system complications (such as stroke and dementia) as a consequence of systemic arterial wall mineralization. In addition, renovascular hypertension and atrial septal aneurysm can be seen in PXE patients.

Conditions in which serum phosphate levels are reduced or elevated are referred to as hypophosphatemia and hyperphosphatemia, respectively. Hypophosphatemia, which often results from renal phosphate wasting, is caused by a number of genetic disorders including X-linked hypophosphatemic rickets (XLH), hereditary hypophosphatemic rickets with hypercakiuria (HHRH), hypophosphatemic bone disease (HBD), and autosomal dominant hypophosphatemic rickets (ADHR). The exact molecular mechanisms by which proper serum phosphate concentrations are maintained are poorly understood.

There is a need in the art for novel compositions and methods for treating diseases and disorders associated with pathological calcification and/or pathological ossification. Such compositions and methods should not undesirably disturb other physiologic processes. Such compositions and methods should reduce the level of calcification and increasing PPi plasma levels in individuals who exhibit lower than normal plasma PPi levels. The present invention fulfills this need.

BRIEF DESCRIPTION OF THE DRAWINGS

The following detailed description of exemplary embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A illustrates time courses of AMP product formation after addition of 50 nM hNPP3 with (from bottom to top) 0.98, 1.95, 3.9, 7.8, 15.6, 31.3, 62.5, 125, 250 and 500 µM ATP. The enzyme reaction was quenched by equal volume of 3 M formic acid at different times, and the reaction product AMP was quantified by HPLC analysis with an AMP standard curve. The smooth line though data points are best fits to a non-linear enzyme kinetic model with product inhibition and substrate depletion. FIG. 1B illustrates steady state ATPase cycling rate comparison. ENPP3 substrate concentration dependence of initial steady state enzyme cycling rate was compared with the previously measured values for human ENPP1. ATPase cycling reaction of both 50 nM hNPP3 and hNPP1 totally depleted ATP substrate in 1 minute for 0.98, 1.95 and 3.9 µM ATP, and thus these three rates were omitted from the plot because their rates could not be accurately determined. The hNPP3 steady state ATPase reaction reached the maximum ($k_{cat}$) of 2.59 (±0.04) s$^{-1}$ enzyme$^{-1}$, from the weighted average of the measured rates with 7.8, 15.6, 31.3, 62.5, 125 µM substrate concentration, seeming slower than that for hNPP1 3.46 (±0.44) s$^{-1}$ enzyme$^{-1}$. The $K_M$ can be estimated <8 µM. At substrate [ATP]>125 µM, hNPP3 ATPase cycling rate gradually decreased. FIG. 1C illustrates substrate concentration dependent η. The decreasing η value with substrate concentration for both enzymes indicates that substrate depletion contributes to the nonlinearity in the enzyme reaction time courses much more than product inhibition at the lower initial substrate concentration. The striking similarity with human ENPP3 vs. human ENPP1 η indicates the two enzymes have similar reaction rate and product inhibition. hNPP1 has slightly faster rate and thus depletes substrate ATP slightly faster than hNPP3 at low substrate concentration.

BRIEF SUMMARY OF THE INVENTION

Figure 1A:
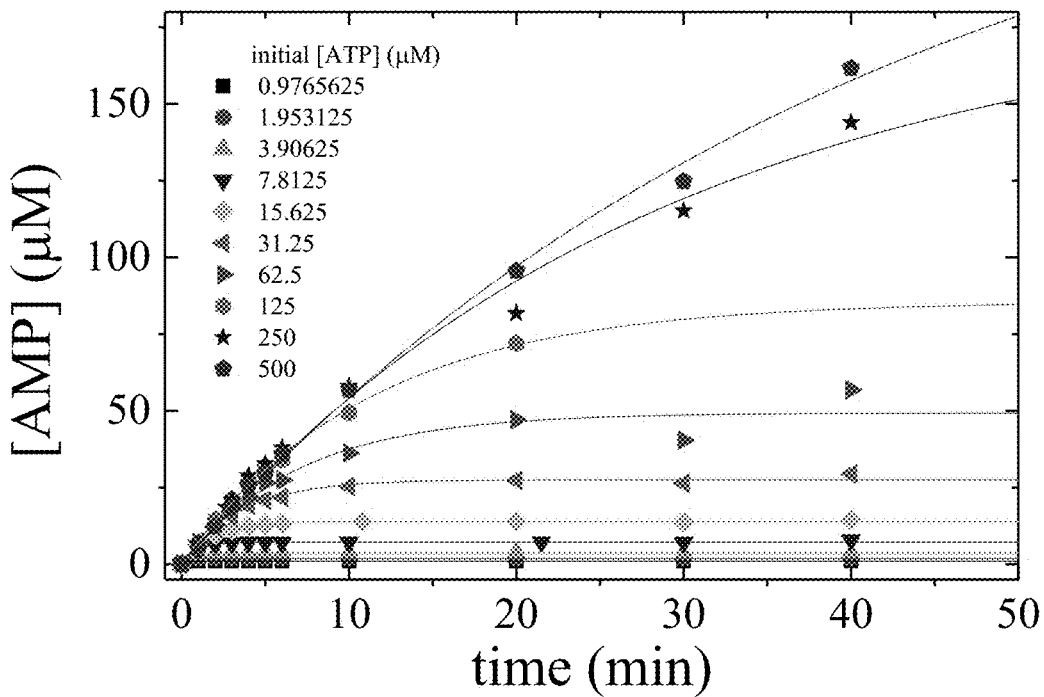
FIGS. 1A-1C comprise graphs illustrating studies of human ENPP3 steady state ATP hydrolysis activity.

The invention provides an isolated polypeptide, or a pharmaceutical salt or solvate thereof. The invention further provides a method of treating or preventing a disease or disorder associated with pathological calcification or pathological ossification in a subject in need thereof. The invention further provides a method of reducing or preventing vascular calcification in a subject with low plasma pyrophosphate (PPi) or high serum phosphate (Pi). The invention further provides a method of treating of a subject having NPP1 deficiency or NPP1-associated disease. The invention further provides a kit comprising at least one isolated polypeptide of the invention and instructions reciting the use of the at least one polypeptide for treating a disease or disorder associated with pathological calcification or pathological ossification in a subject in need thereof, optionally further comprising an applicator.

In certain embodiments, the polypeptide of the invention has formula (I): EXPORT-PROTEIN-Z-DOMAIN-X-Y (I), wherein in (I): EXPORT is absent, or a signal export sequence or a biologically active fragment thereof; PROTEIN is the extracellular domain of ENPP3 (SEQ ID NO: 1) or a biologically active fragment thereof; DOMAIN is selected from the group consisting of a human IgG Fc domain and human albumin domain; X and Z are independently absent or a polypeptide comprising 1-20 amino acids; and, Y is absent or a sequence selected from the group consisting of: (DSS)$_n$ (SEQ ID NO:6), (ESS)$_n$ (SEQ ID NO:7), (RQQ)$_n$ (SEQ ID NO: 8), (KR)$_n$ (SEQ ID NO:9), R$_n$ (SEQ ID NO:10), (KR)$_n$ (SEQ ID NO:11), DSSSEEKFLR-RIGRFG (SEQ ID NO:12), EEEEEEEPRGDT (SEQ ID NO:13), APWHLSSQYSRT (SEQ ID NO:14), STLPIPHEFSRE (SEQ ID NO:15), VTKHLNQISQSY (SEQ ID NO: 16), $E_n$ (SEQ ID NO:17), and $D_n$ (SEQ ID NO:18), wherein each occurrence of n is independently an integer ranging from 1 to 20.

In certain embodiments, the nuclease domain of the PROTEIN or mutant thereof is absent. In other embodiments, EXPORT is absent or selected from the group consisting of SEQ ID NOs: 2-5. In yet other embodiments, X is selected from the group consisting of: absent, a polypeptide consisting of 20 amino acids, a polypeptide consisting of 19 amino acids, a polypeptide consisting of 18 amino acids, a polypeptide consisting of 17 amino acids, a polypeptide consisting of 16 amino acids, a polypeptide consisting of 15 amino acids, a polypeptide consisting of 14 amino acids, a polypeptide consisting of 13 amino acids, a polypeptide consisting of 12 amino acids, a polypeptide consisting of 11 amino acids, a polypeptide consisting of 10 amino acids, a polypeptide consisting of 9 amino acids, a polypeptide consisting of 8 amino acids, a polypeptide consisting of 7 amino acids, a polypeptide consisting of 6 amino acids, a polypeptide consisting of 5 amino acids, a polypeptide consisting of 4 amino acids, a polypeptide consisting of 3 amino acids, a polypeptide consisting of 2 amino acids, and a polypeptide consisting of 1 amino acid. In yet other embodiments, Z is selected from the group consisting of: absent, a polypeptide consisting of 20 amino acids, a polypeptide consisting of 19 amino acids, a polypeptide consisting of 18 amino acids, a polypeptide consisting of 17 amino acids, a polypeptide consisting of 16 amino acids, a polypeptide consisting of 15 amino acids, a polypeptide consisting of 14 amino acids, a polypeptide consisting of 13 amino acids, a polypeptide consisting of 12 amino acids, a polypeptide consisting of 11 amino acids, a polypeptide consisting of 10 amino acids, a polypeptide consisting of 9 amino acids, a polypeptide consisting of 8 amino acids, a polypeptide consisting of 7 amino acids, a polypeptide consisting of 6 amino acids, a polypeptide consisting of 5 amino acids, a polypeptide consisting of 4 amino acids, a polypeptide consisting of 3 amino acids, a polypeptide consisting of 2 amino acids, and a polypeptide consisting of 1 amino acid.

In certain embodiments, DOMAIN is a human IgG Fc domain selected from the group consisting of IgG1, IgG2, IgG3 and IgG4. In other embodiments, the polypeptide is selected from the group consisting of SEQ ID NOs: 19, 21 and 22. In yet other embodiments, DOMAIN is a human albumin domain. In yet other embodiments, the polypeptide is selected from the group consisting of SEQ ID NOs: 24, 25 and 26.

In certain embodiments, the polypeptide comprises a soluble region of NPP3 and lacks a transmembrane domain and a signal peptide, or a fusion protein thereof, wherein the polypeptide reduces cellular calcification when administered to a subject suffering from diseases of calcification and ossification. In other embodiments, the polypeptide comprises a soluble region of NPP3 and lacks a transmembrane domain and a signal peptide, wherein the polypeptide reduces cellular calcification when administered to a subject suffering from diseases of calcification and ossification.

In certain embodiments, the polypeptide comprises the extracellular domain of ENPP3 (SEQ ID NO:1) or a biologically active fragment thereof. In other embodiments, the polypeptide consists essentially of SEQ ID NO:1 or a biologically active fragment thereof. In yet other embodiments, the polypeptide consists of SEQ ID NO: 1 or a biologically active fragment thereof.

In certain embodiments, the soluble ENPP3 fragment or fusion protein thereof comprises the extracellular domain of ENPP3 (SEQ ID NO:1) or a biologically active fragment thereof. In other embodiments, the soluble ENPP3 fragment consists essentially of SEQ ID NO: 1 or a biologically active fragment thereof. In yet other embodiments, the soluble ENPP3 fragment consists of SEQ ID NO: 1 or a biologically active fragment thereof. In yet other embodiments, the soluble ENPP3 fragment or fusion protein thereof lacks a transmembrane domain and a signal peptide.

In certain embodiments, the method comprises administering to the subject a therapeutically effective amount of at least one polypeptide the invention, or a pharmaceutical salt or solvate thereof. In other embodiments, the method comprises administering to the subject a therapeutically effective amount of an isolated recombinant human soluble ENPP3 fragment or fusion protein thereof.

In certain embodiments, the disease or disorder comprises at least one selected from the group consisting of GACI, IIAC, PXE, OPLL, hypophosphatemic rickets, osteoarthritis, calcification of atherosclerotic plaques, hereditary and non-hereditary forms of osteoarthritis, ankylosing spondylitis, hardening of the arteries occurring with aging, and calciphylaxis resulting from end stage renal disease (or mineral bone disorder of chronic kidney disease).

In certain embodiments, the disease or disorder comprises at least one selected from a group consisting of GACI, IIAC, PXE, OPLL, MWVC, ARHR2, ESRD, CKD-MBD, XLH, age related osteopenia, CUA and hypophosphatemic rickets.

In certain embodiments, the disease or disorder is GACI. In other embodiments, the disease or disorder is IIAC. In yet other embodiments, the disease or disorder is PXE. In yet other embodiments, the disease or disorder is OPLL. In yet other embodiments, the disease or disorder is hypophosphatemic rickets. In yet other embodiments, the disease or disorder is osteoarthritis. In yet other embodiments, the disease or disorder is calcification of atherosclerotic plaques. In yet other embodiments, the disease or disorder is hereditary and non-hereditary forms of osteoarthritis. In yet other embodiments, the disease or disorder is ankylosing spondylitis. In yet other embodiments, the disease or disorder is hardening of the arteries occurring with aging. In yet other embodiments, the disease or disorder is calciphylaxis resulting from end stage renal disease (or mineral bone disorder of chronic kidney disease). In yet other embodiments, the disease or disorder is age related osteopenia. In yet other embodiments, the disease or disorder is CUA. In yet other embodiments, the disease or disorder is MWVC. In yet other embodiments, the disease or disorder is ARHR2. In yet other embodiments, the disease or disorder is ESRD.

In certain embodiments, the administered amount raises the level of plasma PPi in the subject to at least about 800 nM. In other embodiments, the administered amount raises the level of plasma PPi in the subject to at least about 1 µM. In yet other embodiments, the administered amount raises the level of plasma PPi in the subject to at least about 1.5 µM.

In certain embodiments, the at least one polypeptide is administered acutely or chronically to the subject. In other embodiments, the at least one polypeptide is administered locally, regionally or systemically to the subject. In yet other embodiments, the subject is a mammal. In yet other embodiments, the mammal is human.

DETAILED DESCRIPTION OF THE INVENTION

The present invention relates to the discovery that ENPP3 (also known as NPP3), which is a member of the ectonucleotide pyrophosphatase/phosphodiesterase (ENPP or NPP) family of enzymes, has potent ATP hydrolase activity. ENPP3 hydrolyzes ATP to AMP and PPi, as demonstrated herein.

In certain aspects, the present invention provides compositions, such as but not limited to fusion proteins, that elevate plasma PPi in physiologic states where plasma PPi is low (as determined, for example, by a medical professional or by consulting of a medical document or manual), placing the individual at risk of morbidity associated with low PPi states. In certain embodiments, these physiologic states are recognized disease conditions such as GACI, PXE, Hutchinson Gilford Progeria Syndrome, chronic kidney disease (CKD), X-linked hypophosphatemia, sickle cell anemia, and end stage renal disease. In other embodiments, these physiologic states occur in non-disease states, such as in elderly adults who are afflicted with chronic ailments known to occur in all aging adults such as "hardening of the arteries" and osteopenia.

In certain embodiments, low plasma PPi is defined as plasma PPi concentration lower than about 1.5 µM. These disease states may or may not be accompanied by pathologic calcification of the arteries and/or soft tissues, medial vascular wall calcifications, strokes or cerebrovascular accidents, decreased pulse wave velocity, calcifications of the soft tissues such as the skin, calcifications of the Bruchs membrane in the eye, calcifications of soft tissues surrounding tendons also known as entheses, calcifications of ligaments in the spine such as the posterior longitudinal ligament, and disease of ossification such as Rickets. In other embodiments, the invention contemplates treatment of low PPi physiologic states via administration of the fusion proteins described herein.

In other aspects, the compositions and methods of the invention can be used to treat disease states known to occur in conditions where the expression or the activity of the enzyme ENPP1 is reduced. These recognized disease states include, in non-limited manner, osteoarthritis, GACI, and ARHR2. These states may also occur in other physiologic states in which ENPP1 protein levels are reduced, such as in individuals who have a common polymporphism in the ENPP1 coding region in which a Q residue is substituted for a K reside at position 121 of the secreted protein (or position 173 of the full length protein) (Eller, et al., 2008, Nephrol. Dial. Transplant. 23 (1): 321-7; Flanagan, et al., 2013, Blood 121 (16): 3237-45).

As demonstrated herein, the products of ATP hydrolysis by ENPP3, and the corresponding enzymatic constants, were analyzed in order to study the enzymatic activity of this enzyme. ENPP3 was found to be a potent ATP hydrolase, capable of generating PPi and AMP from ATP. In certain embodiments, ENPP3 has an ATP hydrolase activity that is comparable to that of ENPP1. As demonstrated herein, ENPP3 catalyzes the hydrolysis of ATP to PPi with nearly the same Michaelis-Menton kinetics as ENPP1, which is another member of the ENPP family of enzymes. In certain embodiments, soluble fusion constructs of ENPP3, including albumin fusion constructs thereof and/or IgG Fc domain constructs thereof, are efficacious in treating diseases of ectopic calcification. In yet other embodiments, the constructs described herein are efficacious in treating and/or preventing disorders of ectopic vascular calcification.

In one aspect, NPP3 is poorly exported to the cell surface. In certain embodiments, soluble ENPP3 protein is constructed by replacing the signal sequence of NPP3 with the native signal sequence of other ENPPs. In other embodiments, soluble ENPP3 constructs are prepared by using the signal export signal sequence of other ENPP enzymes, such as but not limited to ENPP7 and/or ENPP5. In yet other embodiments, soluble ENPP3 constructs are prepared by using a signal sequence comprised of a combination of the signal sequences of ENPP1 and ENPP2 ("ENPP1-2-1" hereinafter). In yet other embodiments, signal sequences of any other known proteins may be used to target the extracellular domain of ENPP3 for secretion as well, such as but not limited to the signal sequence of the immunoglobulin kappa and lambda light chain proteins. Further, the invention should not be construed to be limited to the constructs described herein, but also includes constructs comprising any enzymatically active truncation of the ENPP3 extracellular domain.

Diseases and disorders involving pathological calcification and/or pathological ossification treatable by the compositions and methods of the invention, include, but are not limited to, Idiopathic Infantile Arterial Calcification (IIAC), Ossification of the Posterior Longitudinal Ligament (OPLL), hypophosphatemic rickets, osteoarthritis, calcification of atherosclerotic plaques, Pseudoxanthoma elasticum (PXE), hereditary and non-hereditary forms of osteoarthritis, ankylosing spondylitis, hardening of the arteries occurring with aging, and calciphylaxis resulting from end stage renal disease.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "ADHR" refers to autosomal dominant hypophosphatemic rickets.

As used herein, the term "albumin" refers to the blood plasma protein that is produced in the liver and forms a large proportion of all plasma protein. In certain embodiments, albumin refers to human serum albumin. Usage of other albumins such as bovine serum albumin, equine serum album and porcine serum albumin are also contemplated within the invention.

A disease or disorder is "alleviated" if the severity of a symptom of the disease or disorder, the frequency with which such a symptom is experienced by a patient, or both, is reduced.

As used herein the terms "alteration," "defect," "variation" or "mutation" refer to a mutation in a gene in a cell that affects the function, activity, expression (transcription or translation) or conformation of the polypeptide it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amino acid sequence variant" refers to polypeptides having amino acid sequences that differ to some extent from a native sequence polypeptide. Ordinarily, amino acid sequence variants possess at least about 70% homology, at least about 80% homology, at least about 90% homology, or at least about 95% homology to the native polypeptide. The amino acid sequence variants possess substitutions, deletions, and/or insertions at certain positions within the amino acid sequence of the native amino acid sequence.

As used herein, the term "Ap3P" refers to adenosine-(5')-triphospho-(5')-adenosine or a salt thereof.

As used herein, the term "ARHR2" refers to autosomal recessive hypophosphatemic rickets type-2.

As used herein, the term "CKD" refers to chronic kidney disease.

As used herein, the term "CKD-MBD" refers to chronic kidney disease-bone/mineral disorder.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "composition" or "pharmaceutical composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

As used herein, the term "CUA" refers to calcific uremic arteriolopathy.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties. Specific examples of binding domains include, but are not limited to, DNA binding domains and ATP binding domains.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "ESRD" refers to end-stage renal disease.

As used herein, the term "Fc" refers to a human IgG Fc domain. Subtypes of IgG such as IgG1, IgG2, IgG3, and IgG4 are all being contemplated for usage as Fc domains.

As used herein, the term "fragment," as applied to a nucleic acid, refers to a subsequence of a larger nucleic acid.

A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

As used herein, the term "HBD" refers to hypophosphatemic bone disease.

As used herein, the term "HHRH" refers to hereditary hypophosphatemic rickets with hypercakiuria.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, the term "IIAC" refers to idiopathic infantile arterial calcification.

As used herein, an "immunoassay" refers to any binding assay that uses an antibody capable of binding specifically to a target molecule to detect and quantify the target molecule.

As used herein, the term "immunoglobulin" or "Ig" is defined as a class of proteins that function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody 15 responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Instructional material," as that term is used herein, includes a publication, a recording, a diagram, or any other medium of expression which can be used to communicate the usefulness of the nucleic acid, peptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively. Alternatively, the kit comprises an applicator that can be used to administer the nucleic acid, peptide, and/or compound of the invention to the subject. The application may be for example a drop dispenser, a bottle, a pill dispenser, a syringe and so forth.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "MWVC" refers to medial wall vascular calcification.

As used herein, the term "NPP" refers to ectonucleotide pyrophosphatase/phosphodiesterase.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively (Lehninger, Principles of Biochemistry, at 793-800 (Worth Pub. 1982), which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably herein. When a nucleotide sequence is represented herein by a DNA sequence (e.g., A, T, G, and C), this also includes the corresponding RNA sequence (e.g., A, U, G, C) in which "U" replaces "T."

As used herein, the term "OPLL" refers to ossification of posterior longitudinal ligament.

As used herein, the term "patient," "individual" or "subject" refers to a human or a non-human mammal. Non-human mammals include, for example, livestock and pets, such as ovine, bovine, porcine, canine, feline and murine mammals. Exemplarily, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. "Pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethane sulfonic, p-toluenesulfonic, sulfanilic, cyclohexylaminosulfonic, stearic, alginic, β-hydroxy butyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "plasma pyrophosphate levels" or "plasma PPi" refers to the amount of pyrophosphate (PPi) present in plasma of animals. In certain embodiments, animals include mammals, such as but not limited to rat, mouse, cat, dog, human, cow and horse. In certain embodiments, PPi is measured in plasma rather than serum, because of its release from platelets. There are several non-limiting ways to measure PPi, one of which is by enzymatic assay using uridine-diphosphoglucose (UDPG) pyrophosphorylase as described by Lust and Seegmiller (Lust, et al., 1976, Clin. Chim. Acta 66:241-249; Cheung & Suhadolnik, 1977, Anal. Biochem. 83:61-63) with modifications. Typically healthy individuals exhibit a mean plasma level of about 3.0 µM. The levels of plasma PPi in subjects with aging and or with diseases of calcification or ossification are much lower than the normal levels. In certain embodiments, subjects exhibit a low plasma PPi level of about 1.5 µm. In other embodiments, for subjects with diseases of calcification the plasma PPi levels are about 500 nM, about 600 nM, about 700 nM, about 800 nM, about 900 nM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.2 µM, about 2.4 µM, and/or about 2.6 µM. In yet other embodiments, for subjects with diseases of calcification the plasma PPi levels range from about 500 nM to about 2.8 µM, about 600 nM to about 2.8 µM, about 700 nM to about 2.8 µM, about 800 nM to about 2.8 µM, about 900 nM to about 2.8 µM, about 1 µM to about 2.8 µM, about 1.1 µM to about 2.8 M, about 1.2 µM to about 2.8 µM, about 1.3 µM to about 2.8 µM, about 1.4 µM to about 2.8 µM, about 1.5 µM to about 2.8 µM, about 1.6 µM to about 2.8 µM, about 1.7 µM to about 2.8 µM, about 1.8 µM to about 2.8 µM, about 1.9 µM to about 2.8 µM, about 2 µM to about 2.8 µM, about 2.2 µM to about 2.8 M, about 2.4 µM to about 2.8 µM, and/or about 2.6 µM to about 2.8 µM.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, amino acids are represented by the full name thereof, by the three letter code corresponding thereto, or by the one-letter code corresponding thereto, as indicated below: Aspartic Acid, Asp, D; Glutamic Acid, Glu, E; Lysine, Lys, K; Arginine, Arg, R; Histidine, His, H; Tyrosine, Tyr, Y; Cysteine, Cys, C; Asparagine, Asn, N; Glutamine, Gln, Q; Serine, Ser, S; Threonine, Thr, T; Glycine, Gly, G; Alanine, Ala, A; Valine, Val, V; Leucine, Leu, L; Isoleucine, Ile, I; Methionine, Met, M; Proline, Pro, P; Phenylalanine, Phe, F; Tryptophan, Trp, W.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "PXE" refers to pseudoxanthoma elasticum.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, "substantially purified" refers to being essentially free of other components. For example, a substantially purified polypeptide is a polypeptide which has been separated from other components with which it is normally associated in its naturally occurring state.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "XLH" refers to X-linked hypophosphatemia, X-linked dominant hypophosphatemic rickets, X-linked vitamin D-resistant rickets, and/or X-linked hypophosphatemic rickets.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. Naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

In certain embodiments, the polypeptide of the invention has formula (I): EXPORT-PROTEIN-Z-DOMAIN-X-Y (I), wherein in (I): EXPORT is absent, or a signal export sequence or a biologically active fragment thereof; PROTEIN is the extracellular domain of ENPP3 (SEQ ID NO: 1) or a biologically active fragment thereof; DOMAIN is selected from the group consisting of a human IgG Fc domain and human albumin domain; X and Z are independently absent or a polypeptide comprising 1-20 amino acids; and, Y is absent or a sequence selected from the group consisting of: $(DSS)_n$ (SEQ ID NO:6), $(ESS)_n$ (SEQ ID NO:7), $(RQQ)_n$ (SEQ ID NO: 8), (KR), (SEQ ID NO:9), $R_n$ (SEQ ID NO:10), $(KR)_n$ (SEQ ID NO:11), DSSSEEKFLRRIGRFG (SEQ ID NO:12), EEEEEEEPRGDT (SEQ ID NO:13), APWHLSSQYSRT (SEQ ID NO:14), STLPIPHEFSRE (SEQ ID NO:15), VTKHLNQISQSY (SEQ ID NO:16), $E_n$ (SEQ ID NO:17), and $D_n$ (SEQ ID NO:18), wherein each occurrence of n is independently an integer ranging from 1 to 20.

In certain embodiments, the polypeptide comprises the extracellular domain of ENPP3 (SEQ ID NO:1) or a biologically active fragment (or region) thereof.

In certain embodiments, the polypeptide is soluble. In other embodiments, the nuclease domain of the PROTEIN or mutant thereof is absent. In yet other embodiments, EXPORT is absent or selected from the group consisting of SEQ ID NOs: 2-5. In yet other embodiments, X is selected from the group consisting of: absent, a polypeptide consisting of 20 amino acids, a polypeptide consisting of 19 amino acids, a polypeptide consisting of 18 amino acids, a polypeptide consisting of 17 amino acids, a polypeptide consisting of 16 amino acids, a polypeptide consisting of 15 amino acids, a polypeptide consisting of 14 amino acids, a polypeptide consisting of 13 amino acids, a polypeptide consisting of 12 amino acids, a polypeptide consisting of 11 amino acids, a polypeptide consisting of 10 amino acids, a polypeptide consisting of 9 amino acids, a polypeptide consisting of 8 amino acids, a polypeptide consisting of 7 amino acids, a polypeptide consisting of 6 amino acids, a polypeptide consisting of 5 amino acids, a polypeptide consisting of 4 amino acids, a polypeptide consisting of 3 amino acids, a polypeptide consisting of 2 amino acids, and a polypeptide consisting of 1 amino acid. In yet other embodiments, Z is selected from the group consisting of: absent, a polypeptide consisting of 20 amino acids, a polypeptide consisting of 19 amino acids, a polypeptide consisting of 18 amino acids, a polypeptide consisting of 17 amino acids, a polypeptide consisting of 16 amino acids, a polypeptide consisting of 15 amino acids, a polypeptide consisting of 14 amino acids, a polypeptide consisting of 13 amino acids, a polypeptide consisting of 12 amino acids, a polypeptide consisting of 11 amino acids, a polypeptide consisting of 10 amino acids, a polypeptide consisting of 9 amino acids, a polypeptide consisting of 8 amino acids, a polypeptide consisting of 7 amino acids, a polypeptide consisting of 6 amino acids, a polypeptide consisting of 5 amino acids, a polypeptide consisting of 4 amino acids, a polypeptide consisting of 3 amino acids, a polypeptide consisting of 2 amino acids, and a polypeptide consisting of 1 amino acid.

In certain embodiments, X and Z are independently absent or a polypeptide comprising 1-18 amino acids. In other embodiments, X and Z are independently absent or a polypeptide comprising 1-16 amino acids. In yet other embodiments, X and Z are independently absent or a polypeptide comprising 1-14 amino acids. In yet other embodiments, X and Z are independently absent or a polypeptide comprising 1-12 amino acids. In yet other embodiments, X and Z are independently absent or a polypeptide comprising 1-10 amino acids. In yet other embodiments, X and Z are independently absent or a polypeptide comprising 1-8 amino acids. In yet other embodiments, X and Z are independently absent or a polypeptide comprising 1-6 amino acids. In yet other embodiments, X and Z are independently absent or a polypeptide comprising 1-5 amino acids. In yet other embodiments, X and Z are independently absent or a polypeptide comprising 1-4 amino acids. In yet other embodiments, X and Z are independently absent or a polypeptide comprising 1-3 amino acids. In yet other embodiments, X and Z are independently absent or a polypeptide comprising 1-2 amino acids. In yet other embodiments, X and Z are independently absent or a single amino acid.

In certain embodiments, DOMAIN is a human IgG Fc domain selected from the group consisting of IgG1, IgG2, IgG3 and IgG4. In other embodiments, the polypeptide is selected from the group consisting of SEQ ID NOs: 19, 21 and 22. In yet other embodiments, DOMAIN is a human albumin domain. In yet other embodiments, the polypeptide is selected from the group consisting of SEQ ID NOs: 24, 25 and 26.

In certain embodiments, the soluble polypeptide lacks a transmembrane domain and/or signal peptide. In other embodiments, the soluble polypeptide lacks a transmembrane domain. In yet other embodiments, the soluble polypeptide lacks a signal peptide. In yet other embodiments, the soluble polypeptide lacks a transmembrane domain and signal peptide.

In certain embodiments, the polypeptide comprises a soluble region (or fragment) of NPP3 and lacks a transmembrane domain and a signal peptide, or a fusion protein thereof. In other embodiments, the polypeptide comprises a soluble region of NPP3 and lacks a transmembrane domain and/or a signal peptide. In yet other embodiments, the polypeptide comprises a soluble region of NPP3 and lacks a transmembrane domain. In yet other embodiments, the polypeptide comprises a soluble region of NPP3 and lacks a signal peptide. In yet other embodiments, the polypeptide reduces cellular calcification when administered to a subject suffering from diseases of calcification and ossification.

In certain embodiments, the polypeptide consists essentially of SEQ ID NO: 1 or a biologically active fragment thereof. In other embodiments, the polypeptide consists of SEQ ID NO: 1 or a biologically active fragment thereof.

In certain embodiments, the soluble ENPP3 fragment or fusion protein thereof comprises the extracellular domain of ENPP3 (SEQ ID NO:1) or a biologically active fragment thereof. In other embodiments, the soluble ENPP3 fragment consists essentially of SEQ ID NO: 1 or a biologically active fragment thereof. In yet other embodiments, the soluble ENPP3 fragment consists of SEQ ID NO: 1 or a biologically active fragment thereof. In yet other embodiments, the soluble ENPP3 fragment or fusion protein thereof lacks a transmembrane domain and a signal peptide.

In certain embodiments, the polypeptide of the invention is soluble. In other embodiments, the polypeptide of the invention is a recombinant polypeptide. In yet other embodiments, the polypeptide of the invention is further pegylated.

Methods

The invention provides a method of treating or preventing a disease or disorder associated with pathological calcification or pathological ossification in a subject in need thereof. The invention further provides a method of reducing or preventing vascular calcification in a subject with low plasma pyrophosphate (PPi) or high serum phosphate (Pi). The invention further provides a method of treating of a subject having NPP1 deficiency or NPP1-associated disease. The invention further provides a method of treating or preventing disorders and diseases in a subject where an increased activity or level of ENPP3 polypeptide, fragment, derivative, mutant, or mutant fragment thereof is desirable.

In certain embodiments, the subject is administered a therapeutically effective amount of at least one polypeptide of the invention. In other embodiments, the method comprises administering to the subject a therapeutically effective amount of an isolated recombinant human soluble ENPP3 fragment or fusion protein thereof.

In certain embodiments, the disease or disorder comprises at least one selected from the group consisting of GACI, IIAC, PXE, OPLL, hypophosphatemic rickets, osteoarthritis, calcification of atherosclerotic plaques, hereditary and non-hereditary forms of osteoarthritis, ankylosing spondylitis, hardening of the arteries occurring with aging, and calciphylaxis resulting from end stage renal disease (or mineral bone disorder of chronic kidney disease).

In certain embodiments, the disease or disorder comprises at least one selected from a group consisting of GACI, IIAC, PXE, OPLL, MWVC, ARHR2, ESRD, CKD-MBD, XLH, age related osteopenia, CUA and hypophosphatemic rickets.

In certain embodiments, the disease or disorder is GACI. In other embodiments, the disease or disorder is IIAC. In yet other embodiments, the disease or disorder is PXE. In yet other embodiments, the disease or disorder is OPLL. In yet other embodiments, the disease or disorder is hypophosphatemic rickets. In yet other embodiments, the disease or disorder is osteoarthritis. In yet other embodiments, the disease or disorder is calcification of atherosclerotic plaques. In yet other embodiments, the disease or disorder is hereditary and non-hereditary forms of osteoarthritis. In yet other embodiments, the disease or disorder is ankylosing spondylitis. In yet other embodiments, the disease or disorder is hardening of the arteries occurring with aging. In yet other embodiments, the disease or disorder is calciphylaxis resulting from end stage renal disease (or mineral bone disorder of chronic kidney disease). In yet other embodiments, the disease or disorder is age related osteopenia. In yet other embodiments, the disease or disorder is CUA. In yet other embodiments, the disease or disorder is MWVC. In yet other embodiments, the disease or disorder is ARHR2. In yet other embodiments, the disease or disorder is ESRD.

In certain embodiments, the at least one polypeptide is administered acutely or chronically to the subject. In other embodiments, the at least one polypeptide is administered locally, regionally or systemically to the subject. In yet other embodiments, the subject is a mammal. In yet other embodiments, the mammal is human.

In certain embodiments, the administered amount raises the level of plasma PPi in the subject to at least about 250 nM. In other embodiments, the administered amount raises the level of plasma PPi in the subject to at least about 500 nM. In yet other embodiments, the administered amount raises the level of plasma PPi in the subject to at least about 800 nM. In yet other embodiments, the administered amount raises the level of plasma PPi in the subject to at least about 900 nM. In yet other embodiments, the administered amount raises the level of plasma PPi in the subject to at least about 1 µM. In yet other embodiments, the administered amount raises the level of plasma PPi in the subject to at least about 1.2 µM. In yet other embodiments, the administered amount raises the level of plasma PPi in the subject to at least about 1.4 µM. In yet other embodiments, the administered amount raises the level of plasma PPi in the subject to at least about 1.5 µM. In certain embodiments, the administered amount raises the level of plasma PPi in the subject to at least about 2 µM. In certain embodiments, the administered amount raises the level of plasma PPi in the subject to at least about 4 µM.

One skilled in the art, based upon the disclosure provided herein, would understand that the invention is useful in subjects who, in whole (e.g., systemically) or in part (e.g., locally, tissue, organ), are being, or will be, treated for pathological calcification or ossification. In certain embodiments, the invention is useful in treating or preventing pathological calcification or ossification. The skilled artisan will appreciate, based upon the teachings provided herein, that the diseases and disorders treatable by the compositions and methods described herein encompass any disease or disorder where a decrease in calcification or ossification will promote a positive therapeutic outcome.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that a polypeptide of the invention, or a mutant thereof, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject a polypeptide of the invention, or a mutant thereof as a preventative measure against a disease or disorder.

The invention encompasses administration of a polypeptide of the invention, or a mutant thereof to practice the methods of the invention; the skilled artisan would understand, based on the disclosure provided herein, how to formulate and administer the polypeptide of the invention, or a mutant thereof to a subject. However, the present invention is not limited to any particular method of administration or treatment regimen. This is especially true where it would be appreciated by one skilled in the art, equipped with the disclosure provided herein, including the reduction to practice using an art-recognized model of pathological calcification or ossification, that methods of administering a compound of the invention can be determined by one of skill in the pharmacological arts.

Pharmaceutical Compositions and Formulations

The invention envisions the use of a pharmaceutical composition comprising a polypeptide of the invention within the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between about 0.1% and about 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions are formulated using one or more pharmaceutically acceptable excipients or carriers. In certain embodiments, the pharmaceutical compositions comprise a therapeutically effective amount of the active agent and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed., 1985, Remington's Pharmaceutical Sciences, Mack Publishing Co., Easton, PA, which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent, which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount ranging from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition, which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives (e.g., sodium carboxymethylcellulose, hydroxypropylmethylcellulose, methylcellulose). Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one that comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. For example, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans) buccal, (trans) urethral, vaginal (e.g., trans- and perivaginally), (intra)nasal, and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form. For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation. In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Methods and Materials: Sequences:

```
Methods and Materials: Sequences:

Extracellular domain of ENPP3 (SEQ ID NO: 1)
EKQGSCRKKC FDASFRG
LENCRCDVAC KDRGDCCWDF EDTCVESTRI WMCNKFRCGE TRLEASLCSC SDDCLQRKDC
CADYKSVCQG ETSWLEENCD TAQQSQCPEG FDLPPVILFS MDGFRAEYLY TWDTLMPNIN
KLKTCGIHSK YMRAMYPTKT FPNHYTIVTG LYPESHGIID NNMYDVNLNK NFSLSSKEQN
NPAWWHGQPM WLTAMYQGLK AATYFWPGSE VAINGSFPSI YMPYNGSVPF EERISTLLKW
LDLPKAERPR FYTMYFEEPD SSGHAGGPVS ARVIKALQVV DHAFGMLMEG LKQRNLHNCV
NIILLADHGM DQTYCNKMEY MTDYFPRINF FYMYEGPAPR IRAHNIPHDF FSFNSEEIVR
NLSCRKPDQH FKPYLTPDLP KRLHYAKNVR IDKVHLFVDQ QWLAVRSKSN TNCGGGNHGY
NNEFRSMEAI FLAHGPSFKE KTEVEPFENI EVYNLMCDLL RIQPAPNNGT HGSLNHLLKV
PFYEPSHAEE VSKFSVCGFA NPLPTESLDC FCPHLQNSTQ LEQVNQMLNL TQEEITATVK
VNLPFGRPRV LQKNVDHCLL YHREYVSGFG KAMRMPMWSS YTVPQLGDTS PLPPTVPDCL
RADVRVPPSE SQKCSFYLAD KNITHGFLYP PASNRTSDSQ YDALITSNLV PMYEEFRKMW
DYFHSVLLIK HATERNGVNV VSGPIFDYNY DGHFDAPDEI TKHLANTDVP IPTHYFVVLT
SCKNKSHTPE NCPGWLDVLP FIIPHRPTNV ESCPEGKPEA LWVEERFTAH IARVRDVELL
TGLDFYQDKV QPVSEILQLK TYLPTFETTI Signal sequence ENPP7 (SEQ ID NO: 2)
MRGPAVLLTV ALATLLAPGA Signal sequence ENPP7 (SEQ ID NO: 3)
MRGPAVLLTV ALATLLAPGA GA Signal Sequence ENPP5 (SEQ ID NO: 4)
MTSKFLLVSF ILAALSLSTT FS Signal Sequence ENPP1-2-1 (SEQ ID NO: 5)
M E R D G C A G G G S R G G E G G R A P R E G P
A G N G R D R G R S H A A E A P G D P Q A A A S
L L A P M D V G E E P L E K A A R A R T A K D P
N T Y K I I S L F T F A V G V N I C L G F T A
(singly underlined)-(doubly underlined): Swapped residues with NPP2 residues 1-27 to
give cleavage at the singly underlined-doubly underlined transition SEQ ID NO: 6 (DSS)_n, wherein n is an integer ranging between 1 and 20.

SEQ ID NO: 7 (ESS)_n, wherein n is an integer ranging between 1 and 20.

SEQ ID NO: 8 (RQQ)_n, wherein n is an integer ranging between 1 and 20.

SEQ ID NO: 9 (KR)_n, wherein n is an integer ranging between 1 and 20.

SEQ ID NO: 10 R_n, wherein n is an integer ranging between 1 and 20.

SEQ ID NO: 11 (KR)_n, wherein n is an integer ranging between 1 and 20.
```

SEQ ID NO: 12 DSSSEEKFLRRIGRFG

SEQ ID NO: 13 EEEEEEEPRGDT

SEQ ID NO: 14 APWHLSSQYSRT

SEQ ID NO: 15 STLPIPHEFSRE

SEQ ID NO: 16 VTKHLNQISQSY

SEQ ID NO: 17 $E_n$, wherein n is an integer ranging between 1 and 20.

SEQ ID NO: 18 $D_n$, wherein n is an integer ranging between 1 and 20.

ENPP121-NPP3-Fc sequence (SEQ ID NO: 19)
MERDGCAGGG SRGGEGGRAP REGPAGNGRD RGRSHAAEAP GDPQAAASLL APMDVGEEPL
EKAARARTAK DPNTYKIISL FTFAVGVNIC LGFTAKQGSC RKKCFDASFR GLENCRCDVA
CKDRGDCCWD FEDTCVESTR IWMCNKFRCG ERLEASLCSC SDDCLQRKDC CADYKSVCQG
ETSWLEENCD TAQQSQCPEG FDLPPVILFS MDGFRAEYLY TWDTLMPNIN KLKTCGIHSK
YMRAMYPTKT FPNHYTIVTG LYPESHGIID NNMYDVNLNK NFSLSSKEQN NPAWWHGQPM
WLTAMYQGLK AATYFWPGSE VAINGSFPSI YMPYNGSVPF EERISTLLKW LDLPKAERPR
FYTMYFEEPD SSGHAGGPVS ARVIKALQVV DHAFGMLMEG LKQRNLHNCV NIILLADHGM
DQTYCNKMEY MTDYFPRINF FYMYEGPAPR IRAHNIPHDF FSFNSEEIVR NLSCRKPDQH
FKPYLTPDLP KRLHYAKNVR IDKVHLFVDQ QWLAVRSKSN TNCGGGNHGY NNEFRSMEAI
FLAHGPSFKE KTEVEPFENI EVYNLMCDLL RIQPAPNNGT HGSLNHLLKV PFYEPSHAEE
VSKFSVCGFA NPLPTESLDC FCPHLQNSTQ LEQVNQMLNL TQEEITATVK VNLPFGRPRV
LQKNVDHCLL YHREYVSGFG KAMRMPMWSS YTVPQLGDTS PLPPTVPDCL RADVRVPPSE
SQKCSFYLAD KNITHGFLYP PASNRTSDSQ YDALITSNLV PMYEEFRKMW DYFHSVLLIK
HATERNGVNV VSGPIPFDYNY DGHFDAPDEI TKHLANTDVP IPTHYFVVLT SCKNKSHTPE
NCPGWLDVLP FIIPHRPTNV ESCPEGKPEA LWVEERFTAH IARVRDVELL TGLDFYQDKV
QPVSEILQLK TYLPTFETTI <u>DKTHTCPPCP APELLGGPSV FLFPPKPKDT LMISRTPEVT</u>
<u>CVVVDVSHED PEVKFNWYVD GVEVHNAKTK PREEQYNSTY RVVSVLTVLH QDWLNGKEYK</u>
<u>CKVSNKALPA PIEKTISKAK GQPREPQVYT LPPSREEMTK NQVSLTCLVK GFYPSDIAVE</u>
<u>WESNGQPENN YKTTPPVLDS DGSFFLYSKL TVDKSRWQQG NVFSCSVMHE ALHNHYTQKS</u>
<u>LSLSPGK</u>

Bold residues=amino acid sequence from NPP1; Single underlined residues=signal peptide sequence from NPP2; Double underlined residues=amino acid sequence of IgG Fc domain. In certain embodiments, the IgG Fc domain is selected from any of the subclasses IgG1, IgG2, IgG3 and IgG4. In other embodiments, instead of Fc domain, albumin domain is used.

In certain embodiments, the NPP3 C-terminus and the Fc/albumin domain are connected by a linker. In other embodiments, the linker comprises at least two amino acids. In yet other embodiments, the linker comprises 2-40 amino acids, 2-30 amino acids, 2-20 amino acids, 2-18 amino acids, 2-16 amino acids, 2-14 amino acids, 2-12 amino acids, 2-10 amino acids, 2-8 amino acids, 2-6 amino acids, 2-4 amino acids, or 2 amino acids. In yet other embodiments, the flexible linker comprises a polyethylene glycol chain and/or a hydrocarbon chain (such as an alkylene chain).

IgG Fc sequence
(SEQ ID NO: 20)
DKTHTCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSREEMTK

NQVSLKLVKGFYPSDIAVETNESNGQPENNYKTIPPVLDSDGSFFLYSKLTVDKSRWQQGNVFSCSVMHE

ALHNHYTQKSLSLSPGK

ENPP7-NPP3-Fcsequence
(SEQ ID NO: 21)
<u>MRGPAVLLTV ALATLLAPGA</u> KQGSC RKKCFDASFR GLENCRCDVA

CKDRGDCCWD FEDTCVESTR IWMCNKFRCG ERLEASLCSC SDDCLQRKDC CADYKSVCQG

ETSWLEENCD TAQQSQCPEG FDLPPVILFS MDGFRAEYLY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NLSCRKPDQH

FKPYLTPDLP KRLHYAKNVR IDKVHLFVDQ QWLAVRSKSN TNCGGGNHGY NNEFRSMEAI

```
FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TQEEITATVK VNLPFGRPRV

LQKNVDHCLL YHREYVSGFG KAMRMPMWSS YTVPQLGDTS PLPPTVPDCL RADVRVPPSE

SQKCSFYLAD KNITHGFLYP PASNRTSDSQ YDALITSNLV PMYEEFRKMW DYFHSVLLIK

HATERNGVNV VSGPIFDYNY DGHFDAPDEI TKHLANTDVP IPTHYFVVLT SCKNKSHTPE

NCPGWLDVLP FIIPHRPTNV ESCPEGKPEA LWVEERFTAH IARVRDVELL TGLDFYQDKV

QPVSEILQLK TYLPTFETTI DKTHTCPPCP APELLGGPSV FLFPPKPKDT LMISRTPEVT

CVVVDVSHED PEVKFNWYVD GVEVHNAKTK PREEQYNSTY RVVSVLTVLH QDWLNGKEYK

CKVSNKALPA PIEKTISKAK GQPREPQVYT LPPSREEMTK NQVSLTCLVK GFYPSDIAVE

WESNGQPENN YKTTPPVLDS DGSFFLYSKL TVDKSRWQQG NVFSCSVMHE ALHNHYTQKS

LSLSPGK
```

Single underlined residues=signal peptide sequence from NPP7; Double underlined residues=amino acid sequence of IgG Fc domain. In certain embodiments, the IgG Fc domain is selected from any of the subclasses IgG1, IgG2, IgG3 and IgG4. In other embodiments, instead of Fc domain, albumin domain is used.

In certain embodiments, the NPP3 C-terminus and the Fc/albumin domain are connected by a linker. In other embodiments, the linker comprises at least two amino acids. In yet other embodiments, the linker comprises 2-40 amino acids, 2-30 amino acids, 2-20 amino acids, 2-18 amino acids, 2-16 amino acids, 2-14 amino acids, 2-12 amino acids, 2-10 amino acids, 2-8 amino acids, 2-6 amino acids, 2-4 amino acids, or 2 amino acids. In yet other embodiments, the flexible linker comprises a polyethylene glycol chain and/or a hydrocarbon chain (such as an alkylene chain).

```
ENPP5-NPP3-Fcsequence
                                                      (SEQ ID NO: 22)
MTSKFLLVSF ILAALSLSTT FSKQGSC RKKCFDASFR GLENCRCDVA

CKDRGDCCWD FEDTCVESTR IWMCNKFRCG ERLEASLCSC SDDCLQRKDC CADYKSVCQG

ETSWLEENCD TAQQSQCPEG FDLPPVILFS MDGFRAEYLY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NLSCRKPDQH

FKPYLTPDLP KRLHYAKNVR IDKVHLFVDQ QWLAVRSKSN TNCGGGNHGY NNEFRSMEAI

FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TQEEITATVK VNLPFGRPRV

LQKNVDHCLL YHREYVSGFG KAMRMPMWSS YTVPQLGDTS PLPPTVPDCL RADVRVPPSE

SQKCSFYLAD KNITHGFLYP PASNRTSDSQ YDALITSNLV PMYEEFRKMW DYFHSVLLIK

HATERNGVNV VSGPIFDYNY DGHFDAPDEI TKHLANTDVP IPTHYFVVLT SCKNKSHTPE

NCPGWLDVLP FIIPHRPTNV ESCPEGKPEA LWVEERFTAH IARVRDVELL TGLDFYQDKV

QPVSEILQLK TYLPTFETTI DKTHTCPPCP APELLGGPSV FLFPPKPKDT LMISRTPEVT

CVVVDVSHED PEVKFNWYVD GVEVHNAKTK PREEQYNSTY RVVSVLTVLH QDWLNGKEYK

CKVSNKALPA PIEKTISKAK GQPREPQVYT LPPSREEMTK NQVSLTCLVK GFYPSDIAVE

WESNGQPENN YKTTPPVLDS DGSFFLYSKL TVDKSRWQQG NVFSCSVMHE ALHNHYTQKS

LSLSPGK
```

Single underlined residues=signal peptide sequence from NPP5; Double underlined residues=amino acid sequence of IgG Fc domain. In certain embodiments, the IgG Fc domain is selected from any of the subclasses IgG1, IgG2, IgG3 and IgG4. In other embodiments, instead of Fc domain, albumin domain is used.

In certain embodiments, the NPP3 C-terminus and the Fc/albumin domain are connected by a linker. In other embodiments, the linker comprises at least two amino acids. In yet other embodiments, the linker comprises 2-40 amino acids, 2-30 amino acids, 2-20 amino acids, 2-18 amino acids, 2-16 amino acids, 2-14 amino acids, 2-12 amino acids, 2-10 amino acids, 2-8 amino acids, 2-6 amino acids, 2-4 amino acids, or 2 amino acids. In yet other embodiments, the flexible linker comprises a polyethylene glycol chain and/or a hydrocarbon chain (such as an alkylene chain).

```
Albumin sequence
                                                        (SEQ ID NO: 23)
GGGGSGGGGSGGGGSMKWVTFLLLLFVSGSAFSRGVFRREAHKSEIAHRYNDLGEQHFKGLVLIAFSQYL

QKCSYDEHAKLVQEVTDFAKTCVADESAANCDKSLHTLFGDKLCAIPNLRENYGELADCCTKQEPERNEC

FLQHKDDNPSLPPFERPEAEAMCTSFKENPTTFMGHYLHEVARRHPYFYAPELLYYAEQYNEILTQCCAE

ADKESCLTPKLDGVKEKALVSSVRQRMKCSSMQKFGERAFKAWAVARLSQTFPNADFAEITKLATDLTKV

NKECCHGDLLECADDRAELAKYMCENQATISSKLQTCCDKPLLKKAHCLSEVEHDTMPADLPAIAADFVE

DQEVCKNYAEAKDVFLGTFLYEYSRRHPDYSVSLLLRLAKKYEATLEKCCAEANPPACYGTVLAEFQPLV

EEPKNLVKTNCDLYEKLGEYGFQNAILVRYTQKAPQVSTPTLVEAARNLGRVGTKCCTLPEDQRLPCVED

YLSAILNRVCLLHEKTPVSEHVTKCCSGSLVERRPCFSALTVDETYVPKEFKAETFTFHSDICTLPEKEK

QIKKQTALAELVKHKPKATAEQLKTVMDDFAQFLDTCCKAADKDTCFSTEGPNLVTRCKDALA

ENPP121-NPP3-Albumin sequence
                                                        (SEQ ID NO: 24)
MERDGCAGGG SRGGEGGRAP REGPAGNGRD RGRSHAAEAP GDPQAAASLL APMDVGEEPL

EKAARARTAK DPNTYKIISL FTFAVGVNIC LGFTAKQGSC RKKCFDASFR GLENCRCDVA

CKDRGDCCWD FEDTCVESTR IWMCNKFRCG ERLEASLCSC SDDCLQRKDC CADYKSVCQG

ETSWLEENCD TAQQSQCPEG FDLPPVILFS MDGFRAEYLY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NLSCRKPDQH

FKPYLTPDLP KRLHYAKNVR IDKVHLFVDQ QWLAVRSKSN TNCGGGNHGY NNEFRSMEAI

FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TQEEITATVK VNLPFGRPRV

LQKNVDHCLL YHREYVSGFG KAMRMPMWSS YTVPQLGDTS PLPPTVPDCL RADVRVPPSE

SQKCSFYLAD KNITHGFLYP PASNRTSDSQ YDALITSNLV PMYEEFRKMW DYFHSVLLIK

HATERNGVNV VSGPIFDYNY DGHFDAPDEI TKHLANTDVP IPTHYFVVLT SCKNKSHTPE

NCPGWLDVLP FIIPHRPTNV ESCPEGKPEA LWVEERFTAH IARVRDVELL TGLDFYQDKV

QPVSEILQLK TYLPTFETTI

GGGSGGGGSG GGGSMKWVTF LLLLFVSGSA FSRGVFRREA HKSEIAHRYN DLGEQHFKGL

VLIAFSQYLQ KCSYDEHAKL VQEVTDFAKT CVADESAANC DKSLHTLFGD KLCAIPNLRE

NYGELADCCT KQEPERNECF LQHKDDNPSL PPFERPEAEA MCTSFKENPT TFMGHYLHEV

ARRHPYFYAP ELLYYAEQYN EILTQCCAEA DKESCLTPKL DGVKEKALVS SVRQRMKCSS

MQKFGERAFK AWAVARLSQT FPNADFAEIT KLATDLTKVN KECCHGDLLE CADDRAELAK

YMCENQATIS SKLQTCCDKP LLKKAHCLSE VEHDTMPADL PAIAADFVED QEVCKNYAEA

KDVFLGTFLY EYSRRHPDYS VSLLLRLAKK YEATLEKCCA EANPPACYGT VLAEFQPLVE

EPKNLVKTNC DLYEKLGEYG FQNAILVRYT QKAPQVSTPT LVEAARNLGR VGTKCCTLPE
```

-continued

<u>DQRLPCVEDY LSAILNRVCL LHEKTPVSEH VTKCCSGSLV ERRPCFSALT VDETYVPKEF</u>

<u>KAETFTFHSD ICTLPEKEKQ IKKQTALAEL VKHKPKATAE QLKTVMDDFA QFLDTCCKAA</u>

<u>DKDTCFSTEG PNLVTRCKDA LA</u>

Bold residues=amino acid sequence from NPP1; Single underlined residues=signal peptide sequence from NPP2; Double underlined residues=amino acid sequence of spacer sequence and albumin domain.

In certain embodiments, the NPP3 C-terminus and the albumin domain are connected by a linker. In other embodiments, the linker comprises at least two amino acids. In yet other embodiments, the linker comprises 2-40 amino acids, 2-30 amino acids, 2-20 amino acids, 2-18 amino acids, 2-16 amino acids, 2-14 amino acids, 2-12 amino acids, 2-10 amino acids, 2-8 amino acids, 2-6 amino acids, 2-4 amino acids, or 2 amino acids. In yet other embodiments, the flexible linker comprises a polyethylene glycol chain and/or a hydrocarbon chain (such as an alkylene chain).

ENPP7-NPP3-Albumin sequence
(SEQ ID NO: 25)

<u>MRGPAVLLTV ALATLLAPGA</u> KQGSC RKKCFDASFR GLENCRCDVA

CKDRGDCCWD FEDTCVESTR IWMCNKFRCG ERLEASLCSC SDDCLQRKDC CADYKSVCQG

ETSWLEENCD TAQQSQCPEG FDLPPVILFS MDGFRAEYLY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NLSCRKPDQH

FKPYLTPDLP KRLHYAKNVR IDKVHLFVDQ QWLAVRSKSN TNCGGGNHGY NNEFRSMEAI

FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TQEEITATVK VNLPFGRPRV

LQKNVDHCLL YHREYVSGFG KAMRMPMWSS YTVPQLGDTS PLPPTVPDCL RADVRVPPSE

SQKCSFYLAD KNITHGFLYP PASNRTSDSQ YDALITSNLV PMYEEFRKMW DYFHSVLLIK

HATERNGVNV VSGPIFDYNY DGHFDAPDEI TKHLANTDVP IPTHYFVVLT SCKNKSHTPE

NCPGWLDVLP FIIPHRPTNV ESCPEGKPEA LWVEERFTAH IARVRDVELL TGLDFYQDKV

QPVSEILQLK TYLPTFETTI

<u>GGGSGGGGSG GGGSMKWVTF LLLLFVSGSA FSRGVFRREA HKSEIAHRYN DLGEQHFKGL</u>

<u>VLIAFSQYLQ KCSYDEHAKL VQEVTDFAKT CVADESAANC DKSLHTLFGD KLCAIPNLRE</u>

<u>NYGELADCCT KQEPERNECF LQHKDDNPSL PPFERPEAEA MCTSFKENPT TFMGHYLHEV</u>

<u>ARRHPYFYAP ELLYYAEQYN EILTQCCAEA DKESCLTPKL DGVKEKALVS SVRQRMKCSS</u>

<u>MQKFGERAFK AWAVARLSQT FPNADFAEIT KLATDLTKVN KECCHGDLLE CADDRAELAK</u>

<u>YMCENQATIS SKLQTCCDKP LLKKAHCLSE VEHDTMPADL PAIAADFVED QEVCKNYAEA</u>

<u>KDVFLGTFLY EYSRRHPDYS VSLLLRLAKK YEATLEKCCA EANPPACYGT VLAEFQPLVE</u>

<u>EPKNLVKTNC DLYEKLGEYG FQNAILVRYT QKAPQVSTPT LVEAARNLGR VGTKCCTLPE</u>

<u>DQRLPCVEDY LSAILNRVCL LHEKTPVSEH VTKCCSGSLV ERRPCFSALT VDETYVPKEF</u>

<u>KAETFTFHSD ICTLPEKEKQ IKKQTALAEL VKHKPKATAE QLKTVMDDFA QFLDTCCKAA</u>

<u>DKDTCFSTEG PNLVTRCKDA LA</u>

Single underlined residues=signal peptide sequence from NPP7; Double underlined residues=amino acid sequence of spacer sequence and albumin domain.

In certain embodiments, the NPP3 C-terminus and the albumin domain are connected by a linker. In other embodiments, the linker comprises at least two amino acids. In yet other embodiments, the linker comprises 2-40 amino acids, 2-30 amino acids, 2-20 amino acids, 2-18 amino acids, 2-16 amino acids, 2-14 amino acids, 2-12 amino acids, 2-10 amino acids, 2-8 amino acids, 2-6 amino acids, 2-4 amino acids, or 2 amino acids. In yet other embodiments, the flexible linker comprises a polyethylene glycol chain and/or a hydrocarbon chain (such as an alkylene chain).

```
ENPP5-NPP3-albumin sequence
                                                  (SEQ ID NO: 26)
MTSKFLLVSF ILAALSLSTT FSKQGSC RKKCFDASFR GLENCRCDVA

CKDRGDCCWD FEDTCVESTR IWMCNKFRCG ERLEASLCSC SDDCLQRKDC CADYKSVCQG

ETSWLEENCD TAQQSQCPEG FDLPPVILFS MDGFRAEYLY TWDTLMPNIN KLKTCGIHSK

YMRAMYPTKT FPNHYTIVTG LYPESHGIID NNMYDVNLNK NFSLSSKEQN NPAWWHGQPM

WLTAMYQGLK AATYFWPGSE VAINGSFPSI YMPYNGSVPF EERISTLLKW LDLPKAERPR

FYTMYFEEPD SSGHAGGPVS ARVIKALQVV DHAFGMLMEG LKQRNLHNCV NIILLADHGM

DQTYCNKMEY MTDYFPRINF FYMYEGPAPR IRAHNIPHDF FSFNSEEIVR NLSCRKPDQH

FKPYLTPDLP KRLHYAKNVR IDKVHLFVDQ QWLAVRSKSN TNCGGGNHGY NNEFRSMEAI

FLAHGPSFKE KTEVEPFENI EVYNLMCDLL RIQPAPNNGT HGSLNHLLKV PFYEPSHAEE

VSKFSVCGFA NPLPTESLDC FCPHLQNSTQ LEQVNQMLNL TQEEITATVK VNLPFGRPRV

LQKNVDHCLL YHREYVSGFG KAMRMPMWSS YTVPQLGDTS PLPPTVPDCL RADVRVPPSE

SQKCSFYLAD KNITHGFLYP PASNRTSDSQ YDALITSNLV PMYEEFRKMW DYFHSVLLIK

HATERNGVNV VSGPIFDYNY DGHFDAPDEI TKHLANTDVP IPTHYFVVLT SCKNKSHTPE

NCPGWLDVLP FIIPHRPTNV ESCPEGKPEA LWVEERFTAH IARVRDVELL TGLDFYQDKV

QPVSEILQLK TYLPTFETTI

GGGSGGGGSG GGGSMKWVTF LLLLFVSGSA FSRGVFRREA HKSEIAHRYN DLGEQHFKGL

VLIAFSQYLQ KCSYDEHAKL VQEVTDFAKT CVADESAANC DKSLHTLFGD KLCAIPNLRE

NYGELADCCT KQEPERNECF LQHKDDNPSL PPFERPEAEA MCTSFKENPT TFMGHYLHEV

ARRHPYFYAP ELLYYAEQYN EILTQCCAEA DKESCLTPKL DGVKEKALVS SVRQRMKCSS

MQKFGERAFK AWAVARLSQT FPNADFAEIT KLATDLTKVN KECCHGDLLE CADDRAELAK

YMCENQATIS SKLQTCCDKP LLKKAHCLSE VEHDTMPADL PAIAADFVED QEVCKNYAEA

KDVFLGTFLY EYSRRHPDYS VSLLLRLAKK YEATLEKCCA EANPPACYGT VLAEFQPLVE

EPKNLVKTNC DLYEKLGEYG FQNAILVRYT QKAPQVSTPT LVEAARNLGR VGTKCCTLPE

DQRLPCVEDY LSAILNRVCL LHEKTPVSEH VTKCCSGSLV ERRPCFSALT VDETYVPKEF

KAETFTFHSD ICTLPEKEKQ IKKQTALAEL VKHKPKATAE QLKTVMDDFA QFLDTCCKAA

DKDTCFSTEG PNLVTRCKDA LA
```

Single underlined residues=signal peptide sequence from NPP5; Double underlined residues=amino acid sequence of spacer sequence and albumin domain.

In certain embodiments, the NPP3 C-terminus and the albumin domain are connected by a linker. In other embodiments, the linker comprises at least two amino acids. In yet other embodiments, the linker comprises 2-40 amino acids, 2-30 amino acids, 2-20 amino acids, 2-18 amino acids, 2-16 amino acids, 2-14 amino acids, 2-12 amino acids, 2-10 amino acids, 2-8 amino acids, 2-6 amino acids, 2-4 amino acids, or 2 amino acids. In yet other embodiments, the flexible linker comprises a polyethylene glycol chain and/or a hydrocarbon chain (such as an alkylene chain).

```
Nucleotide sequence of NPP121-NPP3-Fc
                                                      (SEQ ID NO: 27)
ATGGAAAGGGACGGATGCGCCGGTGGTGGATCTCG

CGGAGGCGAAGGTGGAAGGGCCCCTAGGGAAGGACCTGCCGGAAACGGAAGGGACAGGGG

ACGCTCTCACGCCGCTGAAGCTCCAGGCGACCCTCAGGCCGCTGCCTCTCTGCTGGCTCC

TATGGACGTCGGAGAAGAACCCCTGGAAAAGGCCGCCAGGGCCAGGACTGCCAAGGACCC

CAACACCTACAAGATCATCTCCCTCTTCACTTTCGCCGTCGGAGTCAACATCTGCCTGGG

ATTCACCGCCGAAAAGCAAGGCAGCTGCAGGAAGAAGTGCTTTGATGCATCATTTAGAGG

ACTGGAGAACTGCCGGTGTGATGTGGCATGTAAAGACCGAGGTGATTGCTGCTGGGATTT

TGAAGACACCTGTGTGGAATCAACTCGAATATGGATGTGCAATAAATTTCGTTGTGGAGA

GACCAGATTAGAGGCCAGCCTTTGCTCTTGTTCAGATGACTGTTTGCAGAGGAAAGATTG

CTGTGCTGACTATAAGAGTGTTTGCCAAGGAGAAACCTCATGGCTGGAAGAAAACTGTGA

CACAGCCCAGCAGTCTCAGTGCCCAGAAGGGTTTGACCTGCCACCAGTTATCTTGTTTTC

TATGGATGGATTTAGAGCTGAATATTTATACACATGGGATACTTTAATGCCAAATATCAA

TAAACTGAAAACATGTGGAATTCATTCAAAATACATGAGAGCTATGTATCCTACCAAAAC

CTTCCCAAATCATTACACCATTGTCACGGGCTTGTATCCAGAGTCACATGGCATCATTGA

CAATAATATGTATGATGTAAATCTCAACAAGAATTTTTCACTTTCTTCAAAGGAACAAAA

TAATCCAGCCTGGTGGCATGGGCAACCAATGTGGCTGACAGCAATGTATCAAGGTTTAAA

AGCCGCTACCTACTTTTGGCCCGGATCAGAAGTGGCTATAAATGGCTCCTTTCCTTCCAT

ATACATGCCTTACAACGGAAGTGTCCCATTTGAAGAGAGGATTTCTACACTGTTAAAATG

GCTGGACCTGCCCAAAGCTGAAAGACCCAGGTTTTATACCATGTATTTTGAAGAACCTGA

TTCCTCTGGACATGCAGGTGGACCAGTCAGTGCCAGAGTAATTAAAGCCTTACAGGTAGT

AGATCATGCTTTTGGGATGTTGATGGAAGGCCTGAAGCAGCGGAATTTGCACAACTGTGT

CAATATCATCCTTCTGGCTGACCATGGAATGGACCAGACTTATTGTAACAAGATGGAATA

CATGACTGATTATTTTCCCAGAATAAACTTCTTCTACATGTACGAAGGGCCTGCCCCCCG

CATCCGAGCTCATAATATACCTCATGACTTTTTAGTTTTAATTCTGAGGAAATTGTTAG

AAACCTCAGTTGCCGAAAACCTGATCAGCATTTCAAGCCCTATTTGACTCCTGATTTGCC

AAAGCGACTGCACTATGCCAAGAACGTCAGAATCGACAAAGTTCATCTCTTTGTGGATCA

ACAGTGGCTGGCTGTTAGGAGTAAATCAAATACAAATTGTGGAGGAGGCAACCATGGTTA

TAACAATGAGTTTAGGAGCATGGAGGCTATCTTTCTGGCACATGGACCCAGTTTTAAAGA

GAAGACTGAAGTTGAACCATTTGAAAATATTGAAGTCTATAACCTAATGTGTGATCTTCT

ACGCATTCAACCAGCACCAAACAATGGAACCCATGGTAGTTTAAACCATCTTCTGAAGGT

GCCTTTTTATGAGCCATCCCATGCAGAGGAGGTGTCAAAGTTTTCTGTTTGTGGCTTTGC

TAATCCATTGCCCACAGAGTCTCTTGACTGTTTCTGCCCTCACCTACAAAATAGTACTCA

GCTGGAACAAGTGAATCAGATGCTAAATCTCACCCAAGAAGAAATAACAGCAACAGTGAA

AGTAAATTTGCCATTTGGGAGGCCTAGGGTACTGCAGAAGAACGTGGACCACTGTCTCCT

TTACCACAGGGAATATGTCAGTGGATTTGGAAAAGCTATGAGGATGCCCATGTGGAGTTC
```

-continued
ATACACAGTCCCCCAGTTGGGAGACACATCGCCTCTGCCTCCCACTGTCCCAGACTGTCT

GCGGGCTGATGTCAGGGTTCCTCCTTCTGAGAGCCAAAAATGTTCCTTCTATTTAGCAGA

CAAGAATATCACCCACGGCTTCCTCTATCCTCCTGCCAGCAATAGAACATCAGATAGCCA

ATATGATGCTTTAATTACTAGCAATTTGGTACCTATGTATGAAGAATTCAGAAAAATGTG

GGACTACTTCCACAGTGTTCTTCTTATAAAACATGCCACAGAAAGAAATGGAGTAAATGT

GGTTAGTGGACCAATATTTGATTATAATTATGATGGCCATTTTGATGCTCCAGATGAAAT

TACCAAACATTTAGCCAACACTGATGTTCCCATCCCAACACACTACTTTGTGGTGCTGAC

CAGTTGTAAAAACAAGAGCCACACACCGGAAAACTGCCCTGGGTGGCTGGATGTCCTACC

CTTTATCATCCCTCACCGACCTACCAACGTGGAGAGCTGTCCTGAAGGTAAACCAGAAGC

TCTTTGGGTTGAAGAAAGATTTACAGCTCACATTGCCCGGGTCCGTGATGTAGAACTTCT

CACTGGGCTTGACTTCTATCAGGATAAAGTGCAGCCTGTCTCTGAAATTTTGCAACTAAA

GACATATTTACCAACATTTGAAACCACTATTGACAAAACTCACACATGCCCACCGTGCCC

AGCACCTGAACTCCTGGGGGGACCGTCAGTCTTCCTCTTCCCCCCAAAACCCAAGGACAC

CCTCATGATCTCCCGGACCCCTGAGGTCACATGCGTGGTGGTGGACGTGAGCCACGAAGA

CCCTGAGGTCAAGTTCAACTGGTACGTGGACGGCGTGGAGGTGCATAATGCCAAGACAAA

GCCGCGGGAGGAGCAGTACAACAGCACGTACCGTGTGGTCAGCGTCCTCACCGTCCTGCA

CCAGGACTGGCTGAATGGCAAGGAGTACAAGTGCAAGGTCTCCAACAAAGCCCTCCCAGC

CCCCATCGAGAAAACCATCTCCAAAGCCAAAGGGCAGCCCCGAGAACCACAGGTGTACAC

CCTGCCCCCATCCCGGGAGGAGATGACCAAGAACCAGGTCAGCCTGACCTGCCTGGTCAA

AGGCTTCTATCCCAGCGACATCGCCGTGGAGTGGGAGAGCAATGGGCAGCCGGAGAACAA

CTACAAGACCACGCCTCCCGTGCTGGACTCCGACGGCTCCTTCTTCCTCTATAGCAAGCT

CACCGTGGACAAGAGCAGGTGGCAGCAGGGGAACGTCTTCTCATGCTCCGTGATGCATGA

GGCTCTGCACAACCACTACACGCAGAAGAGCCTCTCCCTGTCCCCGGGTAAA

Nucleotide sequence of NPP121-NPP3-Fc
(SEQ ID NO: 28)
ATGGAAAGGGACGGATGCGCCGGTGGTGGATCTCGCGGAGGCGAAGGTGGAAGGGCCCCT

AGGGAAGGACCTGCCGGAAACGGAAGGGACAGGGGACGCTCTCACGCCGCTGAAGCTCCA

GGCGACCCTCAGGCCGCTGCCTCTCTGCTGGCTCCTATGGACGTCGGAGAAGAACCCCTG

GAAAAGGCCGCCAGGGCCAGGACTGCCAAGGACCCCAACACCTACAAGATCATCTCCCTC

TTCACTTTCGCCGTCGGAGTCAACATCTGCCTGGGATTCACCGCCGAAAAGCAAGGCAGC

TGCAGGAAGAAGTGCTTTGATGCATCATTTAGAGGACTGGAGAACTGCCGGTGTGATGTG

GCATGTAAAGACCGAGGTGATTGCTGCTGGGATTTTGAAGACACCTGTGTGGAATCAACT

CGAATATGGATGTGCAATAAATTTCGTTGTGGAGAGACCAGATTAGAGGCCAGCCTTTGC

TCTTGTTCAGATGACTGTTTGCAGAGGAAAGATTGCTGTGCTGACTATAAGAGTGTTTGC

CAAGGAGAAACCTCATGGCTGGAAGAAAACTGTGACACAGCCCAGCAGTCTCAGTGCCCA

GAAGGGTTTGACCTGCCACCAGTTATCTTGTTTTCTATGGATGGATTTAGAGCTGAATAT

TTATACACATGGGATACTTTAATGCCAAATATCAATAAACTGAAAACATGTGGAATTCAT

TCAAAATACATGAGAGCTATGTATCCTACCAAAACCTTCCCAAATCATTACACCATTGTC

ACGGGCTTGTATCCAGAGTCACATGGCATCATTGACAATAATATGTATGATGTAAATCTC

AACAAGAATTTTTCACTTTCTTCAAAGGAACAAAATAATCCAGCCTGGTGGCATGGGCAA

CCAATGTGGCTGACAGCAATGTATCAAGGTTTAAAAGCCGCTACCTACTTTTGGCCCGGA

TCAGAAGTGGCTATAAATGGCTCCTTTCCTTCCATATACATGCCTTACAACGGAAGTGTC

-continued

```
CCATTTGAAGAGAGGATTTCTACACTGTTAAAATGGCTGGACCTGCCCAAAGCTGAAAGA

CCCAGGTTTTATACCATGTATTTTGAAGAACCTGATTCCTCTGGACATGCAGGTGGACCA

GTCAGTGCCAGAGTAATTAAAGCCTTACAGGTAGTAGATCATGCTTTTGGGATGTTGATG

GAAGGCCTGAAGCAGCGGAATTTGCACAACTGTGTCAATATCATCCTTCTGGCTGACCAT

GGAATGGACCAGACTTATTGTAACAAGATGGAATACATGACTGATTATTTTCCCAGAATA

AACTTCTTCTACATGTACGAAGGGCCTGCCCCCCGCATCCGAGCTCATAATATACCTCAT

GACTTTTTTAGTTTTAATTCTGAGGAAATTGTTAGAAACCTCAGTTGCCGAAAACCTGAT

CAGCATTTCAAGCCCTATTTGACTCCTGATTTGCCAAAGCGACTGCACTATGCCAAGAAC

GTCAGAATCGACAAAGTTCATCTCTTTGTGGATCAACAGTGGCTGGCTGTTAGGAGTAAA

TCAAATACAAATTGTGGAGGAGGCAACCATGGTTATAACAATGAGTTTAGGAGCATGGAG

GCTATCTTTCTGGCACATGGACCCAGTTTTAAAGAGAAGACTGAAGTTGAACCATTTGAA

AATATTGAAGTCTATAACCTAATGTGTGATCTTCTACGCATTCAACCAGCACCAAACAAT

GGAACCCATGGTAGTTTAAACCATCTTCTGAAGGTGCCTTTTTATGAGCCATCCCATGCA

GAGGAGGTGTCAAAGTTTTCTGTTTGTGGCTTTGCTAATCCATTGCCCACAGAGTCTCTT

GACTGTTTCTGCCCTCACCTACAAAATAGTACTCAGCTGGAACAAGTGAATCAGATGCTA

AATCTCACCCAAGAAGAAATAACAGCAACAGTGAAAGTAAATTTGCCATTTGGGAGGCCT

AGGGTACTGCAGAAGAACGTGGACCACTGTCTCCTTTACCACAGGGAATATGTCAGTGGA

TTTGGAAAAGCTATGAGGATGCCCATGTGGAGTTCATACACAGTCCCCCAGTTGGGAGAC

ACATCGCCTCTGCCTCCCACTGTCCCAGACTGTCTGCGGGCTGATGTCAGGGTTCCTCCT

TCTGAGAGCCAAAAATGTTCCTTCTATTTAGCAGACAAGAATATCACCCACGGCTTCCTC

TATCCTCCTGCCAGCAATAGAACATCAGATAGCCAATATGATGCTTTAATTACTAGCAAT

TTGGTACCTATGTATGAAGAATTCAGAAAAATGTGGGACTACTTCCACAGTGTTCTTCTT

ATAAAACATGCCACAGAAAGAAATGGAGTAAATGTGGTTAGTGGACCAATATTTGATTAT

AATTATGATGGCCATTTTGATGCTCCAGATGAAATTACCAAACATTTAGCCAACACTGAT

GTTCCCATCCCAACACACTACTTTGTGGTGCTGACCAGTTGTAAAAACAAGAGCCACACA

CCGGAAAACTGCCCTGGGTGGCTGGATGTCCTACCCTTTATCATCCCTCACCGACCTACC

AACGTGGAGAGCTGTCCTGAAGGTAAACCAGAAGCTCTTTGGGTTGAAGAAAGATTTACA

GCTCACATTGCCCGGGTCCGTGATGTAGAACTTCTCACTGGGCTTGACTTCTATCAGGAT

AAAGTGCAGCCTGTCTCTGAAATTTTGCAACTAAAGACATATTTACCAACATTTGAAACC

ACTATTGGTGGAGGAGGCTCTGGTGGAGGCGGTAGCGGAGGCGGAGGGTCGATGAAGTGG

GTAACCTTTATTTCCCTTCTTTTTCTCTTTAGCTCGGCTTATTCCAGGGGTGTGTTTCGT

CGAGATGCACACAAGAGTGAGGTTGCTCATCGGTTTAAAGATTTGGGAGAAGAAAATTTC

AAAGCCTTGGTGTTGATTGCCTTTGCTCAGTATCTTCAGCAGTGTCCATTTGAAGATCAT

GTAAAATTAGTGAATGAAGTAACTGAATTTGCAAAAACATGTGTTGCTGATGAGTCAGCT

GAAAATTGTGACAAATCACTTCATACCCTTTTGGAGACAAATTATGCACAGTTGCAACT

CTTCGTGAAACCTATGGTGAAATGGCTGACTGCTGTGCAAAACAAGAACCTGAGAGAAAT

GAATGCTTCTTGCAACACAAAGATGACAACCCAAACCTCCCCCGATTGGTGAGACCAGAG

GTTGATGTGATGTGCACTGCTTTTCATGACAATGAAGAGACATTTTTGAAAAAATACTTA

TATGAAATTGCCAGAAGACATCCTTACTTTTATGCCCCGGAACTCCTTTTCTTTGCTAAA

AGGTATAAAGCTGCTTTTACAGAATGTTGCCAAGCTGCTGATAAAGCTGCCTGCCTGTTG
```

-continued

```
CCAAAGCTCGATGAACTTCGGGATGAAGGGAAGGCTTCGTCTGCCAAACAGAGACTCAAG

TGTGCCAGTCTCCAAAAATTTGGAGAAAGAGCTTTCAAAGCATGGGCAGTAGCTCGCCTG

AGCCAGAGATTTCCCAAAGCTGAGTTTGCAGAAGTTTCCAAGTTAGTGACAGATCTTACC

AAAGTCCACACGGAATGCTGCCATGGAGATCTGCTTGAATGTGCTGATGACAGGGCGGAC

CTTGCCAAGTATATCTGTGAAAATCAAGATTCGATCTCCAGTAAACTGAAGGAATGCTGT

GAAAAACCTCTGTTGGAAAAATCCCACTGCATTGCCGAAGTGGAAAATGATGAGATGCCT

GCTGACTTGCCTTCATTAGCTGCTGATTTTGTTGAAAGTAAGGATGTTTGCAAAAACTAT

GCTGAGGCAAAGGATGTCTTCCTGGGCATGTTTTTGTATGAATATGCAAGAAGGCATCCT

GATTACTCTGTCGTGCTGCTGCTGAGACTTGCCAAGACATATGAAACCACTCTAGAGAAG

TGCTGTGCCGCTGCAGATCCTCATGAATGCTATGCCAAAGTGTTCGATGAATTTAAACCT

CTTGTGGAAGAGCCTCAGAATTTAATCAAACAAAATTGTGAGCTTTTTGAGCAGCTTGGA

GAGTACAAATTCCAGAATGCGCTATTAGTTCGTTACACCAAGAAAGTACCCCAAGTGTCA

ACTCCAACTCTTGTAGAGGTCTCAAGAAACCTAGGAAAAGTGGGCAGCAAATGTTGTAAA

CATCCTGAAGCAAAAAGAATGCCCTGTGCAGAAGACTATCTATCCGTGGTCCTGAACCAG

TTATGTGTGTTGCATGAGAAAACGCCAGTAAGTGACAGAGTCACCAAATGCTGCACAGAA

TCCTTGGTGAACAGGCGACCATGCTTTTCAGCTCTGGAAGTCGATGAAACATACGTTCCC

AAAGAGTTTAATGCTGAAACATTCACCTTCCATGCAGATATATGCACACTTTCTGAGAAG

GAGAGACAAATCAAGAAACAAACTGCACTTGTTGAGCTCGTGAAACACAAGCCCAAGGCA

ACAAAAGAGCAACTGAAAGCTGTTATGGATGATTTCGCAGCTTTTGTAGAGAAGTGCTGC

AAGGCTGACGATAAGGAGACCTGCTTTGCCGAGGAGGGTAAAAAACTTGTTGCTGCAAGT

CAAGCTGCCTTAGGCTTA
```

Nucleotide sequence of hNPP3-hFc-pcDNA3
(SEQ ID NO: 29)
```
GACGGATCGGGAGATCTCCCGATCCCCTATGGTCGACTCTCAGTACAATCTGCTCTGATG

CCGCATAGTTAAGCCAGTATCTGCTCCCTGCTTGTGTGTTGGAGGTCGCTGAGTAGTGCG

CGAGCAAAATTTAAGCTACAACAAGGCAAGGCTTGACCGACAATTGCATGAAGAATCTGC

TTAGGGTTAGGCGTTTTGCGCTGCTTCGCGATGTACGGGCCAGATATACGCGTTGACATT

GATTATTGACTAGTTATTAATAGTAATCAATTACGGGGTCATTAGTTCATAGCCCATATA

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGACTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTGATGCGGTTTTGGCAGTACATCAATGGGCGTGGATAGCGGTTTG

ACTCACGGGGATTTCCAAGTCTCCACCCCATTGACGTCAATGGGAGTTTGTTTTGGCACC

AAAATCAACGGGACTTTCCAAAATGTCGTAACAACTCCGCCCCATTGACGCAAATGGGCG

GTAGGCGTGTACGGTGGGAGGTCTATATAAGCAGAGCTCTCTGGCTAACTAGAGAACCCA

CTGCTTACTGGCTTATCGAAATTAATACGACTCACTATAGGGAGACCCAAGCTTATGGAA

AGGGACGGATGCGCCGGTGGTGGATCTCGCGGAGGCGAAGGTGGAAGGGCCCCTAGGGAA

GGACCTGCCGGAAACGAAGGGACAGGGGACGCTCTCACGCCGCTGAAGCTCCAGGCGAC

CCTCAGGCCGCTGCCTCTCTGCTGGCTCCTATGGACGTCGGAGAAGAACCCCTGGAAAAG

GCCGCCAGGGCCAGGACTGCCAAGGACCCCAACACCTACAAGATCATCTCCCTCTTCACT
```

-continued

```
TTCGCCGTCGGAGTCAACATCTGCCTGGGATTCACCGCCGAAAAGCAAGGCAGCTGCAGG

AAGAAGTGCTTTGATGCATCATTTAGAGGACTGGAGAACTGCCGGTGTGATGTGGCATGT

AAAGACCGAGGTGATTGCTGCTGGGATTTTGAAGACACCTGTGTGGAATCAACTCGAATA

TGGATGTGCAATAAATTTCGTTGTGGAGAGACCAGATTAGAGGCCAGCCTTTGCTCTTGT

TCAGATGACTGTTTGCAGAGGAAAGATTGCTGTGCTGACTATAAGAGTGTTTGCCAAGGA

GAAACCTCATGGCTGGAAGAAAACTGTGACACAGCCCAGCAGTCTCAGTGCCCAGAAGGG

TTTGACCTGCCACCAGTTATCTTGTTTTCTATGGATGGATTTAGAGCTGAATATTTATAC

ACATGGGATACTTTAATGCCAAATATCAATAAACTGAAAACATGTGGAATTCATTCAAAA

TACATGAGAGCTATGTATCCTACCAAAACCTTCCCAAATCATTACACCATTGTCACGGGC

TTGTATCCAGAGTCACATGGCATCATTGACAATAATATGTATGATGTAAATCTCAACAAG

AATTTTTCACTTTCTTCAAAGGAACAAAATAATCCAGCCTGGTGGCATGGGCAACCAATG

TGGCTGACAGCAATGTATCAAGGTTTAAAAGCCGCTACCTACTTTTGGCCCGGATCAGAA

GTGGCTATAAATGGCTCCTTTCCTTCCATATACATGCCTTACAACGGAAGTGTCCCATTT

GAAGAGAGGATTTCTACACTGTTAAAATGGCTGGACCTGCCCAAAGCTGAAAGACCCAGG

TTTTATACCATGTATTTTGAAGAACCTGATTCCTCTGGACATGCAGGTGGACCAGTCAGT

GCCAGAGTAATTAAAGCCTTACAGGTAGTAGATCATGCTTTTGGGATGTTGATGGAAGGC

CTGAAGCAGCGGAATTTGCACAACTGTGTCAATATCATCCTTCTGGCTGACCATGGAATG

GACCAGACTTATTGTAACAAGATGGAATACATGACTGATTATTTTCCCAGAATAAACTTC

TTCTACATGTACGAAGGGCCTGCCCCCCGCATCCGAGCTCATAATATACCTCATGACTTT

TTTAGTTTTAATTCTGAGGAAATTGTTAGAAACCTCAGTTGCCGAAAACCTGATCAGCAT

TTCAAGCCCTATTTGACTCCTGATTTGCCAAAGCGACTGCACTATGCCAAGAACGTCAGA

ATCGACAAAGTTCATCTCTTTGTGGATCAACAGTGGCTGGCTGTTAGGAGTAAATCAAAT

ACAAATTGTGGAGGAGGCAACCATGGTTATAACAATGAGTTTAGGAGCATGGAGGCTATC

TTTCTGGCACATGGACCCAGTTTTAAAGAGAAGACTGAAGTTGAACCATTTGAAAATATT

GAAGTCTATAACCTAATGTGTGATCTTCTACGCATTCAACCAGCACCAAACAATGGAACC

CATGGTAGTTTAAACCATCTTCTGAAGGTGCCTTTTTATGAGCCATCCCATGCAGAGGAG

GTGTCAAAGTTTTCTGTTTGTGGCTTTGCTAATCCATTGCCCACAGAGTCTCTTGACTGT

TTCTGCCCTCACCTACAAAATAGTACTCAGCTGGAACAAGTGAATCAGATGCTAAATCTC

ACCCAAGAAGAAATAACAGCAACAGTGAAAGTAAATTTGCCATTTGGGAGGCCTAGGGTA

CTGCAGAAGAACGTGGACCACTGTCTCCTTTACCACAGGGAATATGTCAGTGGATTTGGA

AAAGCTATGAGGATGCCCATGTGGAGTTCATACACAGTCCCCCAGTTGGGAGACACATCG

CCTCTGCCTCCCACTGTCCCAGACTGTCTGCGGGCTGATGTCAGGGTTCCTCCTTCTGAG

AGCCAAAAATGTTCCTTCTATTTAGCAGACAAGAATATCACCCACGGCTTCCTCTATCCT

CCTGCCAGCAATAGAACATCAGATAGCCAATATGATGCTTTAATTACTAGCAATTTGGTA

CCTATGTATGAAGAATTCAGAAAAATGTGGGACTACTTCCACAGTGTTCTTCTTATAAAA

CATGCCACAGAAAGAAATGGAGTAAATGTGGTTAGTGGACCAATATTTGATTATAATTAT

GATGGCCATTTTGATGCTCCAGATGAAATTACCAAACATTTAGCCAACACTGATGTTCCC

ATCCCAACACACTACTTTGTGGTGCTGACCAGTTGTAAAAACAAGAGCCACACACCGGAA

AACTGCCCTGGGTGGCTGGATGTCCTACCCTTTATCATCCCTCACCGACCTACCAACGTG

GAGAGCTGTCCTGAAGGTAAACCAGAAGCTCTTTGGGTTGAAGAAAGATTTACAGCTCAC
```

-continued

```
ATTGCCCGGGTCCGTGATGTAGAACTTCTCACTGGGCTTGACTTCTATCAGGATAAAGTG

CAGCCTGTCTCTGAAATTTTGCAACTAAAGACATATTTACCAACATTTGAAACCACTATT

GACAAAACTCACACATGCCCACCGTGCCCAGCACCTGAACTCCTGGGGGACCGTCAGTC

TTCCTCTTCCCCCCAAAACCCAAGGACACCCTCATGATCTCCCGGACCCCTGAGGTCACA

TGCGTGGTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTCCAAAGCCAAA

GGGCAGCCCCGAGAACCACAGGTGTACACCCTGCCCCCATCCCGGGAGGAGATGACCAAG

AACCAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGG

AACGTCTTCTCATGCTCCGTGATGCATGAGGCTCTGCACAACCACTACACGCAGAAGAGC

CTCTCCCTGTCCCCGGGTAAATGAAATTCTGCAGATATCCATCACACTGGCGGCCGCTCG

AGCATGCATCTAGAGGGCCCTATTCTATAGTGTCACCTAAATGCTAGAGCTCGCTGATCA

GCCTCGACTGTGCCTTCTAGTTGCCAGCCATCTGTTGTTTGCCCCTCCCCCGTGCCTTCC

TTGACCCTGGAAGGTGCCACTCCCACTGTCCTTTCCTAATAAAATGAGGAAATTGCATCG

CATTGTCTGAGTAGGTGTCATTCTATTCTGGGGGGTGGGGTGGGGCAGGACAGCAAGGGG

GAGGATTGGGAAGACAATAGCAGGCATGCTGGGGATGCGGTGGGCTCTATGGCTTCTGAG

GCGGAAAGAACCAGCTGGGGCTCTAGGGGGTATCCCCACGCGCCCTGTAGCGGCGCATTA

AGCGCGGCGGGTGTGGTGGTTACGCGCAGCGTGACCGCTACACTTGCCAGCGCCCTAGCG

CCCGCTCCTTTCGCTTTCTTCCCTTCCTTTCTCGCCACGTTCGCCGGCTTTCCCCGTCAA

GCTCTAAATCGGGGCATCCCTTTAGGGTTCCGATTTAGTGCTTTACGGCACCTCGACCCC

AAAAAACTTGATTAGGGTGATGGTTCACGTAGTGGGCCATCGCCCTGATAGACGGTTTTT

CGCCCTTTGACGTTGGAGTCCACGTTCTTTAATAGTGGACTCTTGTTCCAAACTGGAACA

ACACTCAACCCTATCTCGGTCTATTCTTTTGATTTATAAGGGATTTTGGGGATTTCGGCC

TATTGGTTAAAAAATGAGCTGATTTAACAAAAATTTAACGCGAATTAATTCTGTGGAATG

TGTGTCAGTTAGGGTGTGGAAAGTCCCCAGGCTCCCCAGGCAGGCAGAAGTATGCAAAGC

ATGCATCTCAATTAGTCAGCAACCAGGTGTGGAAAGTCCCCAGGCTCCCCAGCAGGCAGA

AGTATGCAAAGCATGCATCTCAATTAGTCAGCAACCATAGTCCCGCCCCTAACTCCGCCC

ATCCCGCCCCTAACTCCGCCCAGTTCCGCCCATTCTCCGCCCCATGGCTGACTAATTTTT

TTTATTTATGCAGAGGCCGAGGCCGCCTCTGCCTCTGAGCTATTCCAGAAGTAGTGAGGA

GGCTTTTTTGGAGGCCTAGGCTTTTGCAAAAAGCTCCCGGGAGCTTGTATATCCATTTTC

GGATCTGATCAAGAGACAGGATGAGGATCGTTTCGCATGATTGAACAAGATGGATTGCAC

GCAGGTTCTCCGGCCGCTTGGGTGGAGAGGCTATTCGGCTATGACTGGGCACAACAGACA

ATCGGCTGCTCTGATGCCGCCGTGTTCCGGCTGTCAGCGCAGGGGCGCCCGGTTCTTTTT

GTCAAGACCGACCTGTCCGGTGCCCTGAATGAACTGCAGGACGAGGCAGCGCGGCTATCG

TGGCTGGCCACGACGGGCGTTCCTTGCGCAGCTGTGCTCGACGTTGTCACTGAAGCGGGA

AGGGACTGGCTGCTATTGGGCGAAGTGCCGGGGCAGGATCTCCTGTCATCTCACCTTGCT

CCTGCCGAGAAAGTATCCATCATGGCTGATGCAATGCGGCGGCTGCATACGCTTGATCCG

GCTACCTGCCCATTCGACCACCAAGCGAAACATCGCATCGAGCGAGCACGTACTCGGATG
```

-continued

```
GAAGCCGGTCTTGTCGATCAGGATGATCTGGACGAAGAGCATCAGGGGCTCGCGCCAGCC
GAACTGTTCGCCAGGCTCAAGGCGCGCATGCCCGACGGCGAGGATCTCGTCGTGACCCAT
GGCGATGCCTGCTTGCCGAATATCATGGTGGAAAATGGCCGCTTTTCTGGATTCATCGAC
TGTGGCCGGCTGGGTGTGGCGGACCGCTATCAGGACATAGCGTTGGCTACCCGTGATATT
GCTGAAGAGCTTGGCGGCGAATGGGCTGACCGCTTCCTCGTGCTTTACGGTATCGCCGCT
CCCGATTCGCAGCGCATCGCCTTCTATCGCCTTCTTGACGAGTTCTTCTGAGCGGGACTC
TGGGGTTCGAAATGACCGACCAAGCGACGCCCAACCTGCCATCACGAGATTTCGATTCCA
CCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAG
CTTATAATGGTTACAAATAAAGCAATAGCATCACAAATTTCACAAATAAAGCATTTTTTT
CACTGCATTCTAGTTGTGGTTTGTCCAAACTCATCAATGTATCTTATCATGTCTGTATAC
CGTCGACCTCTAGCTAGAGCTTGGCGTAATCATGGTCATAGCTGTTTCCTGTGTGAAATT
GTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGT
CGGGAAACCTGTCGTGCCAGCTGCATTAATGAATCGGCCAACGCGCGGGGAGAGGCGGTT
TGCGTATTGGGCGCTCTTCCGCTTCCTCGCTCACTGACTCGCTGCGCTCGGTCGTTCGGC
TGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGG
CCGCGTTGCTGGCGTTTTTCCATAGGCTCCGCCCCCCTGACGAGCATCACAAAAATCGAC
GCTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCCT
TTCTCCCTTCGGGAAGCGTGGCGCTTTCTCAATGCTCACGCTGTAGGTATCTCAGTTCGG
TGTAGGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGT
TCTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTG
CTGCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCT
CCGGTTCCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGA
```

```
-continued
CTGGTGAGTACTCAACCAAGTCATTCTGAGAATAGTGTATGCGGCGACCGAGTTGCTCTT

GCCCGGCGTCAATACGGGATAATACCGCGCCACATAGCAGAACTTTAAAAGTGCTCATCA

TTGGAAAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGACACGGA

AATGTTGAATACTCATACTCTTCCTTTTTCAATATTATTGAAGCATTTATCAGGGTTATT

GTCTCATGAGCGGATACATATTTGAATGTATTTAGAAAAATAAACAAATAGGGGTTCCGC

GCACATTTCCCCGAAAAGTGCCACCTGACGTC
```

Example 1

Figure 1B:
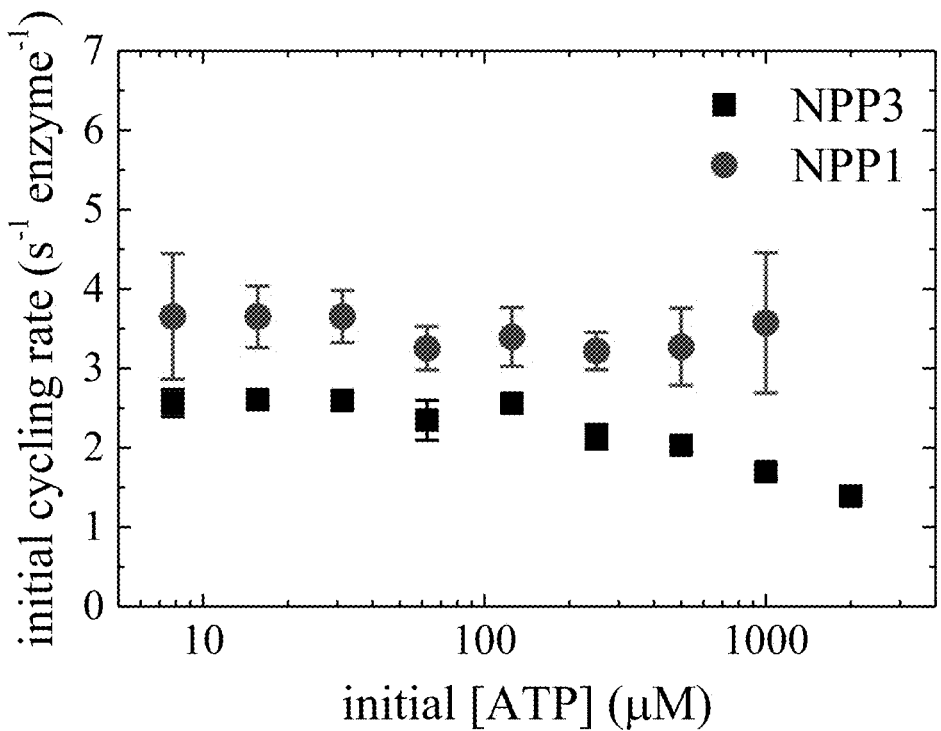
Figure 1C:
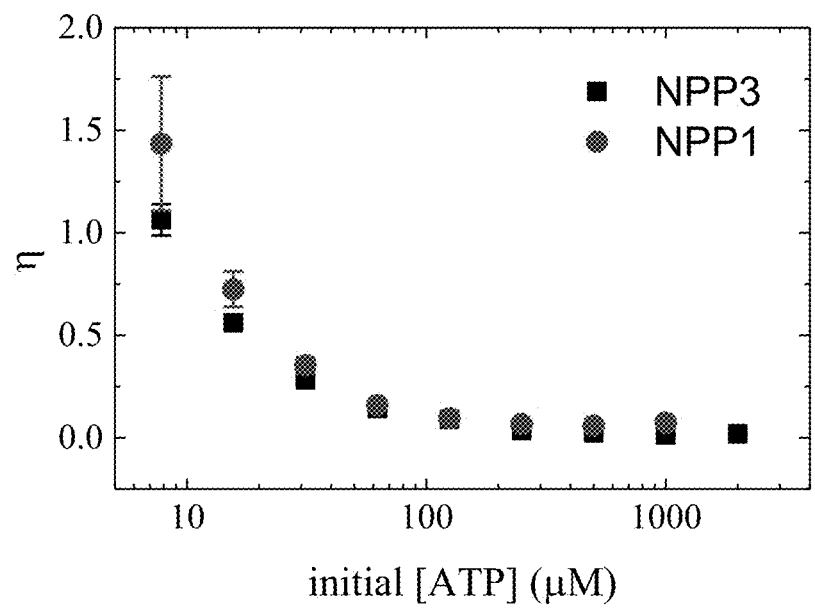

FIGS. 1A-1C comprise graphs illustrating studies of hNPP3 steady state ATP hydrolysis activity.

As illustrated in FIG. 1A, time courses of AMP product formation after addition of 50 nM hNPP3 with (from bottom to top) 0.98, 1.95, 3.9, 7.8, 15.6, 31.3, 62.5, 125, 250 or 500 µM ATP were analyzed. The enzyme reaction was quenched with equal volume of 3 M formic acid at different times and the reaction product, AMP, was quantified by HPLC analysis with an AMP standard curve. The smooth line through the data points were best fits to a non-linear enzyme kinetic model with product inhibition and substrate depletion.

FIG. 1B illustrates steady state ATPase cycling rate comparison. hNPP3 substrate concentration dependence of initial steady state enzyme cycling rate was compared with that measured for hNPP1. ATPase cycling reaction of both 50 nM hNPP3 and hNPP1 depleted ATP substrate within 1 minute at 0.98, 1.95 and 3.9 µM ATP. The uncertainty at these low ATP concentrations was significant, and thus these three rates were omitted from the data set during fitting. The hNPP3 steady state ATPase reaction reached the maximum ($k_{cat}$) of 2.59 (±0.04) s$^{-1}$ enzyme$^{-1}$, from the weighted average of the measured rates at 7.8, 15.6, 31.3, 62.5, 125 µM substrate. The turnover rate of hNPP1 was 3.46 (±0.44) s$^{-1}$ enzyme$^{-1}$. The $K_M$ for ATP substrate was estimated to be <8 µM.

FIG. 1C illustrates substrate concentration dependence of the n value. The decreasing η value with substrate concentration for both enzymes indicates that substrate depletion contributes to the non-linearity in the enzyme reaction time courses much more than product inhibition at lower initial substrate concentrations. The similarity of hNPP3 and hNPP1 n values was consistent with the two enzymes having similar reaction rates and product inhibition.

Example 2: Animal Models

The following non-limiting animal models can be used to test the efficacy of the presently claimed compositions on human disease resulting from low pyrophosphate (PPi):
1. enpplasj/asj model of Generalized Arterial Calcification of Infancy (GACI); Li, et al., 2013, Disease Models & Mech. 6 (5): 1227-35.
2. enpp12asj/2asj model of Generalized Arterial Calcification of Infancy (GACI); Li, et al., 2014, PloS one 9 (12): e113542.
3. ABCC6−/− mouse model of Pseudoxanthoma Elasticum (PXE); Jiang, et al., 2007, J. Invest. Derm. 127 (6): 1392-402.
4. HYP mouse model of X-linked hypophosphatasia (XLH); Liang, et al., 2009, Calcif. Tissue Int. 85 (3): 235-46.
5. LmnaG609G/+ mouse model of Hutchison-Gilford Progeria Syndrome; Villa-Bellosta, et al., 2013, Circulation 127 (24): 2442-51.
6. Tip toe walking (ttw) mouse model of Ossification of the Posterior Longitudinal Ligament (OPLL) (Okawa, et al., 1998, Nature Genetics 19 (3): 271-3; Nakamura, et al., 1999, Human Genetics 104 (6): 492-7) and osteoarthritis (Bertrand, et al., 2012, Annals Rheum. Diseases 71 (7): 1249-53).
7 Rat model of chronic kidney disease (CKD) on the adenine diet; Schibler, et al., 1968, Clin. Sci. 35 (2): 363-72; O'Neill, et al., 2011, Kidney Int. 79 (5): 512-7.
8. Mouse model of chronic kidney disease (CKD) on the adenine diet; Jia, et al., 2013, BMC Nephrol. 14:116.
9. ⅚th nephrectomy rat model of CKD; Morrison, 1962, Lab Invest. 11:321-32; Shimamura & Morrison, 1975, Am. J. Pathol. 79 (1): 95-106.
10. ENPP1 knockout mouse model of GACI and osteopenia; Mackenzie, et al., 2012, PloS one 7 (2): e32177.

In certain embodiments, there is no rodent model that recapitulates the adult form of the human disease GACI, also referred to in the literature as Autosomal Recessive Hypohposphatemic Rickets type 2 (ARHR2) (Levy-Litan, et al., 2010, Am. J. Human Gen. 86 (2): 273-8.

Experimental details on enzymatic activity, quantification of plasma PPi, micro-CT scans, quantification of plasma pyrophosphate uptake and mouse models of calcification are described in detail in the patent applications and/or publications PCT/US2016/33236, WO2014126965 (relating to PCT Patent Application No. PCT/US2014/015945), and US 20150359858, each of which is herein incorporated in its entirety by reference.

Example 3: Production and Purification of ENPP3 Fusion Proteins

Figure 4:
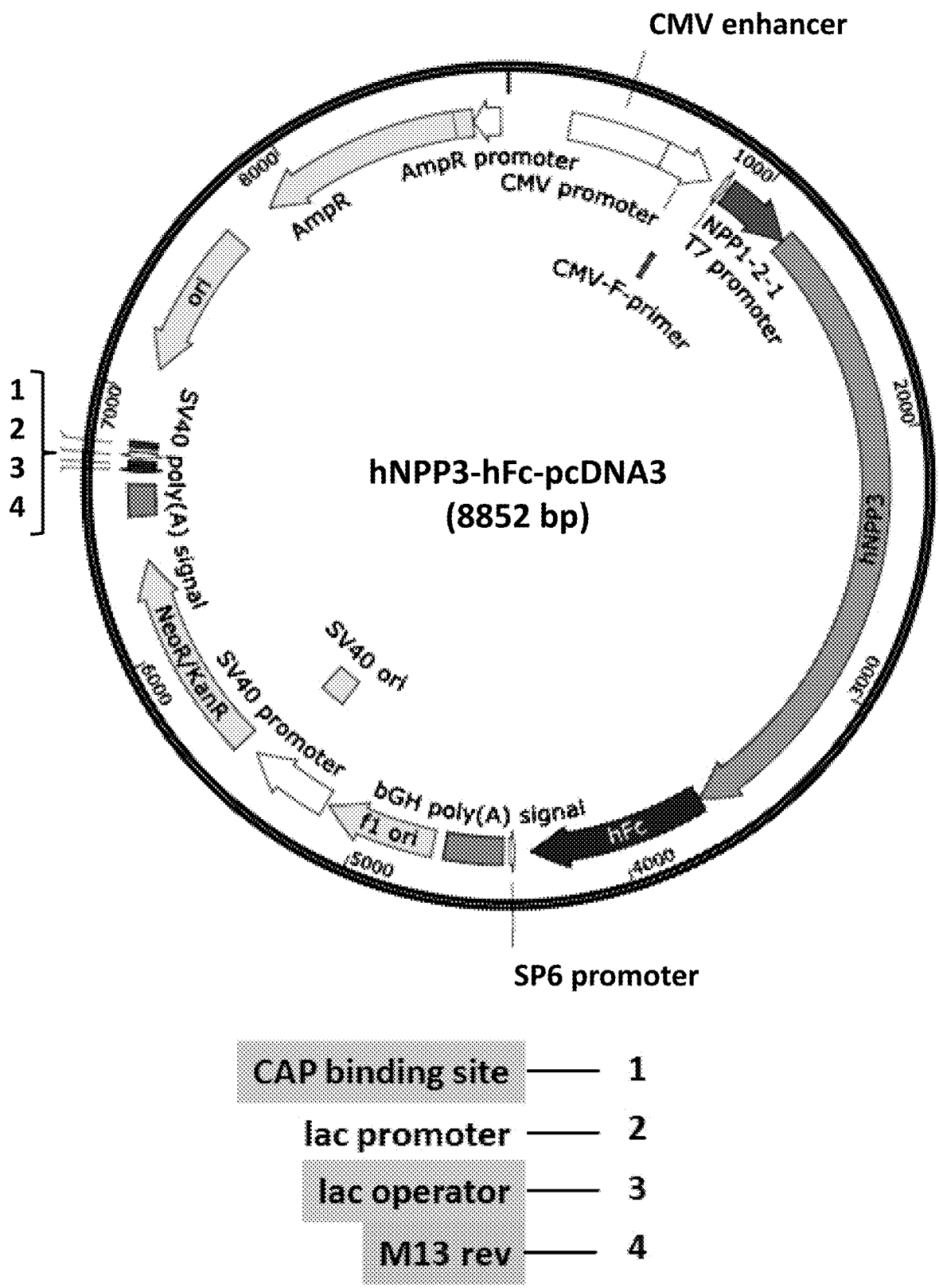
FIG. 4 illustrates a non-limiting plasmid construct map of human NPP121-NPP3-Fc in the plasmid pcDNA3, cloned using IN-FUSION® technology.
Figure 5:
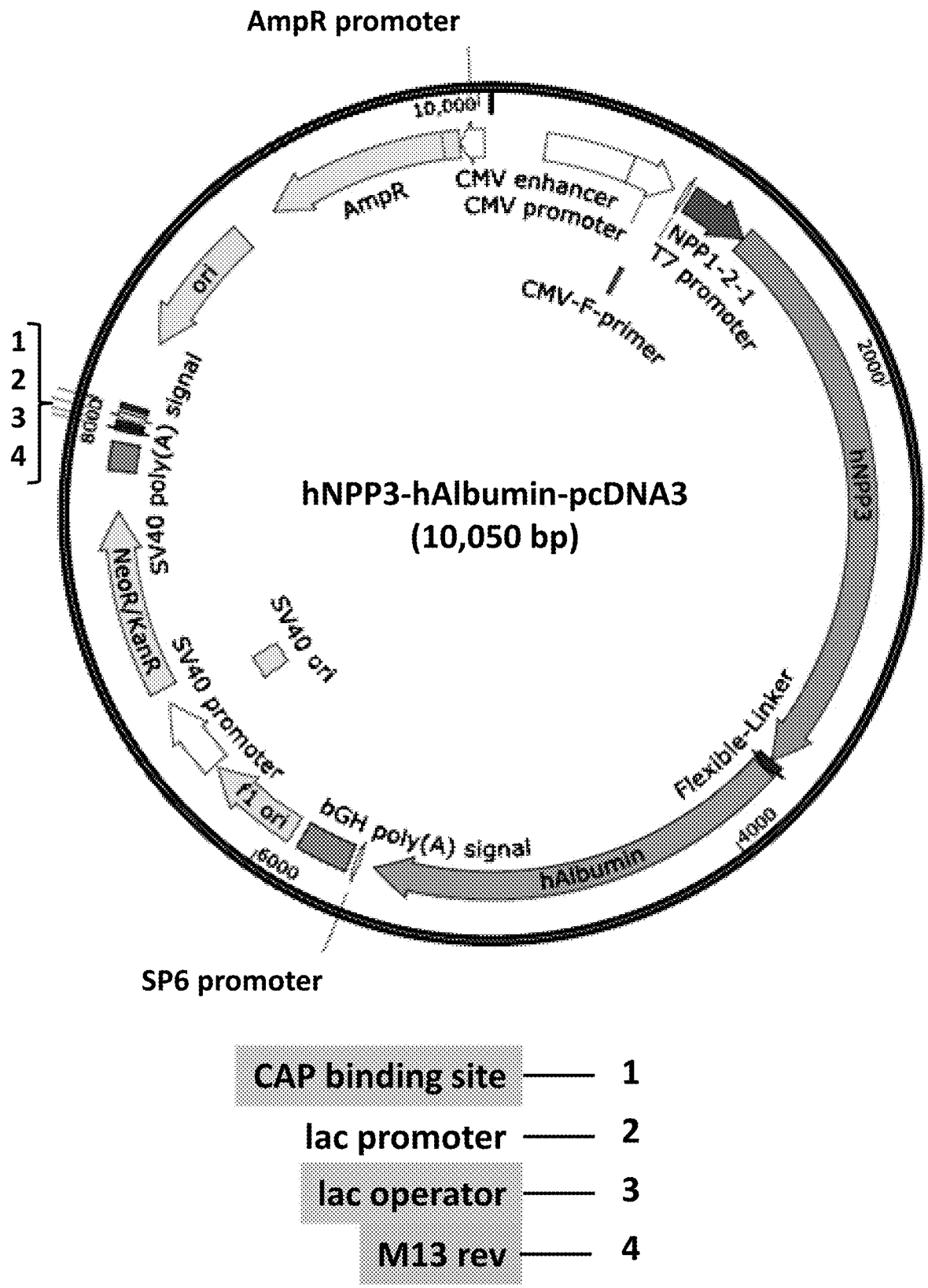
FIG. 5 illustrates a non-limiting plasmid construct map of human NPP121-NPP3-Albumin in the plasmid pcDNA3.

ENPP3 is produced by establishing stable transfections in either CHO or HEK293 mammalian cells. The protein can be produced in either adherent or suspension cells. To establish stable cell lines the nucleic acid sequence encoding NPP3 fusion proteins (FIGS. 3-5 & SEQ ID NO:s 1-29) into an appropriate vector for large scale protein production. There are a variety of these vectors available from commercial sources and any of those can be used.

Figure 3:
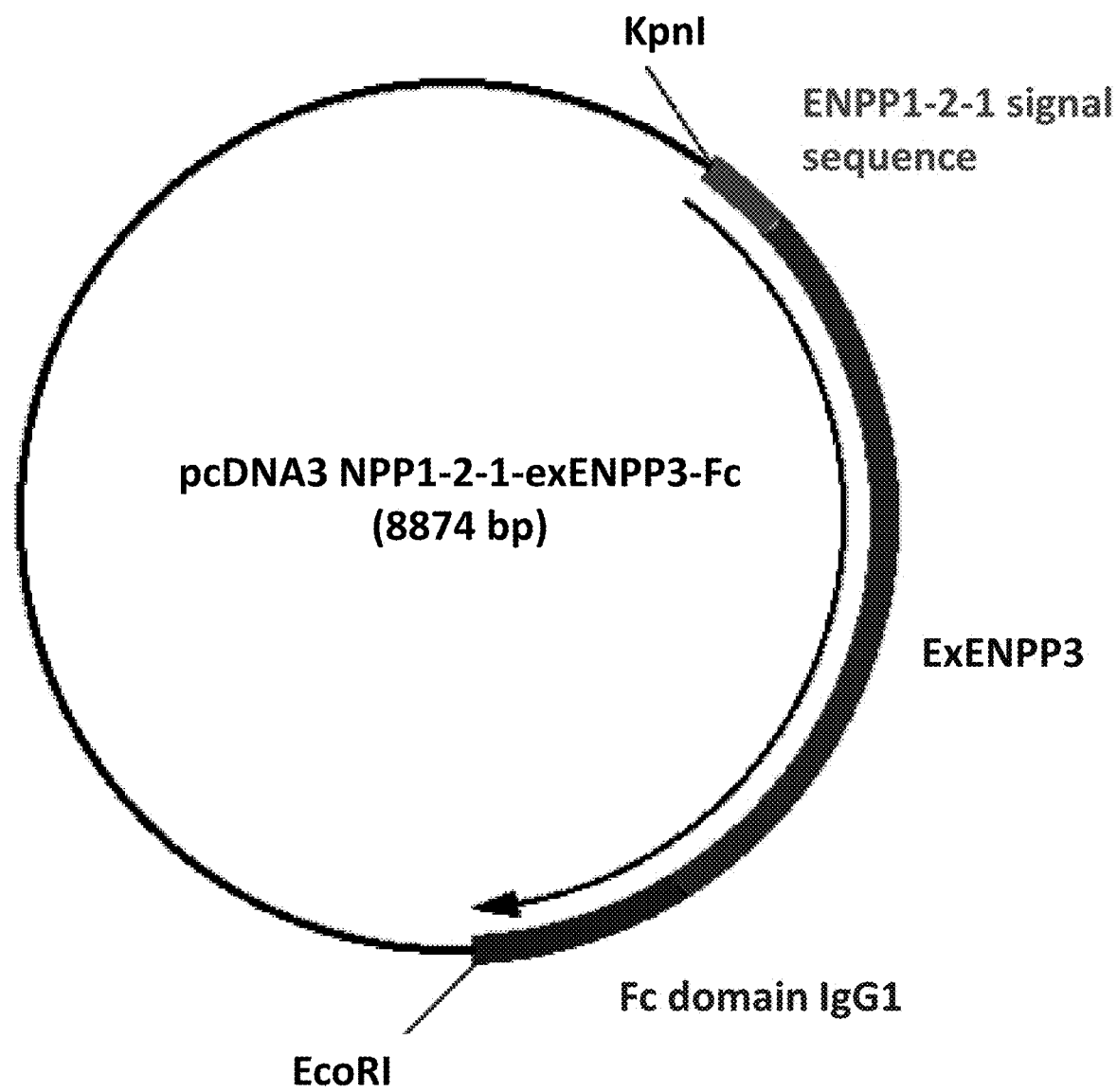
FIG. 3 illustrates a non-limiting plasmid construct map of human NPP121-NPP3-Fc in the plasmid, cloned using the indicated restriction endonuclease sites.

For example, FIG. 3 illustrates a plasmid map of ENPP1-2-1-exENPP3-Fc cloned into the pcDNA3 plasmid with appropriate endonuclease restriction sites. The protein subdomains are color coded to illustrate the signal sequence, extracellular domain of ENPP3, and Fc domains of the fusion protein. The amino acid sequence of the cloned protein is also displayed below the plasmid map and also color coded to illustrate the domains of the fusion protein.

The pcDNA3 plasmid containing the desired protein constructs can be stably transfected into expression plasmid using established techniques such as electroporation or lipofectamine, and the cells can be grown under antibiotic selection to enhance for stably transfected cells.

Clones of single, stably transfected cells are then established and screened for high expressing clones of the desired fusion protein. Screening of the single cell clones for ENPP3 protein expression can be accomplished in a high-throughput manner in 96 well plates using the synthetic enzymatic substrate pNP-TMP as previously described for ENPP1 (Saunders, et al., 2008, Mol. Cancer Therap. 7 (10): 3352-62; Albright, et al., 2015, Nat Commun. 6:10006). Upon identification of high expressing clones through screening, protein production can be accomplished in shaking flasks or bio-reactors previously described for ENPP1 (Albright, et al., 2015, Nat Commun. 6:10006).

Purification of ENPP3 can be accomplished using a combination of standard purification techniques known in the art. These techniques are well known in art and are selected from techniques such as column chromatograph, ultracentrifugation, filtration, and precipitation. Column chromatographic purification is accomplished using affinity chromatography such as protein-A and protein-G resins, metal affinity resins such as nickel or copper, hydrophobic exchange chromatography, and reverse-phase high-pressure chromatography (HPLC) using C8-C14 resins. Ion exchange may also be employed, such as anion and cation exchange chromatography using commercially available resins such as Q-sepharose (anion exchange) and SP-sepharose (cation exchange), blue sepharose resin and blue-sephadex resin, and hydroxyapatite resins. Size exclusion chromatography using commercially available S-75 and S200 Superdex resins can also be employed, as known in the art. Buffers used to solubilize the protein, and provide the selection media for the above described chromatographic steps, are standard biological buffers known to practitioners of the art and science of protein chemistry.

Figure 2:
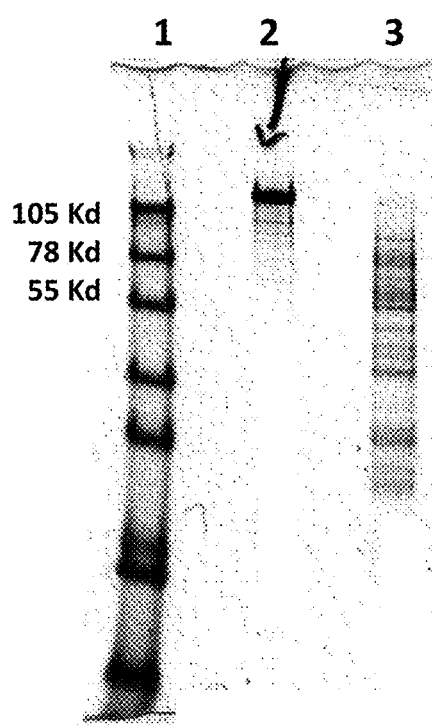
FIG. 2 illustrates a non-limiting purification profile of NPP3 fusion protein through a Coomasie stained sodium dodecyl sulfate polyacrylamide gel electrophoresis (SDS-PAGE) gel, wherein the purified NPP3 protein is shown in relation to certain size markers.

Some examples of buffers that are used in preparation include citrate, phosphate, acetate, tris(hydroxymethyl)aminomethane, saline buffers, glycine-HCL buffers, Cacodylate buffers, and sodium barbital buffers, which are well known in art. Using a single techniques, or a series of techniques in combination, and the appropriate buffer systems adjusted to the appropriate pH, one can purify the fusion proteins described to greater than 99% purity from crude material (see, for example, FIG. 2). This figure compares partially purified ENPP3 and the crude starting material side by side on a Coomasie stained polyacrylamide gel after a single purification step. As demonstrated in FIG. 2, a protein of molecular weight slightly greater than 105 kD corresponding to the appropriate molecular weight of ENPP3 was enriched from the crude starting material displayed in the right lane after a single purification step. This material can then be additionally purified using additional techniques and/or chromatographic steps as described above, to reach substantially higher purity such as ~99% purity. In certain embodiments, the purified protein has enzymatic activity comparable to the enzymatic activity described and demonstrated in FIGS. 1A-1C.

Example 4: Usage of Plasma PPi as a Biomarker

Certain embodiments of the invention contemplate the usage of plasma pyrophosphate as a biomarker to determine which individuals are at risk for diseases of ectopic calcification of the soft tissues, calcification of the medial vascular wall, low bone mineral density, osteopenia, stroke, arthritis, and/or hereditary forms of rickets. Plasma PPi has not been clinically used to predict individuals at risk for the above disorders, as demonstrated by the lack of a plasma PPi test in catalogs of laboratory tests offered by leading clinical laboratories, such as Mayo Medical Laboratory (www dot mayomedicallaboratories dot com/test-catalog/alphabetical/P) or Yale University, or leading commercial reference laboratories such as ARUP (ltd dot aruplab dot com/Search/Browse/P) or The Quest Diagnostics Nichols Institute (www dot specialtylabs dot com/about_us/).

In certain embodiments, plasma PPi has clinical utility as a predictive and diagnostic agent to identify individuals at risk for the above disorders of calcification, ossification, stroke, osteopenia, low bone mineral density, and/or arthritis.

The measurement of plasma PPi can be accomplished by several published methods including radio-isotopic (Cheung, et al., 1977, Anal. Biochem. 83 (1): 61-3) and fluorescent (Jansen, et al., 2013, PNAS USA 110 (50): 20206-11; Jansen, et al., 2014, Arterioscler. Thromb. Vasc. Biol. 34 (9): 1985-9). Correct measurement of plasma PPi requires that platelets are removed from the plasma and that the whole blood, when collected, is not hemolyzed. Platelets can be removed from the blood either by high speed centrifugation or by ultrafiltration. Removal of platelets is required to prevent platelets from releasing PPi and ATP into the plasma upon activation and degranulation, which will artificially elevate the plasma PPi levels. Hemolysis of whole blood also releases ATP into the plasma and falsely elevate the measurement of plasma PPi. Plasma that has been collected from non-hemolyzed blood and removed of platelets can be used to reliable measure PPi concentrations, and can provide clinical utility as predictive diagnostic identifying patients at risk for the above mentioned disorders.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating pathological calcification of soft tissue in a subject in need thereof,
the method comprising administering to the subject a therapeutically effective amount of a polypeptide comprising a soluble ecto-nucleotide pyrophosphate/phosphodiesterase-3 (ENPP3) polypeptide, whereby pathological calcification in the subject is treated.

2. The method of claim 1, wherein the polypeptide is administered locally, regionally, parenterally, or systemically to the subject.

3. The method of claim 1, wherein the polypeptide is administered to the subject in a dosage ranging from about 1 ng/kg to about 500 mg/kg of body weight.

4. The method of claim 1, wherein the polypeptide is administered daily, or more than once per day, or every other day, or weekly, or biweekly, or monthly, to the subject.

5. The method of claim 1, wherein the polypeptide comprises soluble human ENPP3 comprising a C-terminal domain selected from the group consisting of a human IgG Fc domain and human serum albumin.

6. The method of claim 5, wherein the human IgG is selected from the group consisting of IgG1, IgG2, IgG3, and IgG4.

7. The method of claim 5, wherein the polypeptide is selected from the group consisting of SEQ ID NOs: 19, 21, and 22.

8. The method of claim 5, wherein the extracellular domain of ENPP3 comprises amino acid residues of SEQ ID NO: 1.

9. The method of claim 5, wherein the polypeptide is selected from the group consisting of SEQ ID NOs: 24, 25, and 26.

10. The method of claim 1, wherein the pathological calcification of soft tissue is present in a disease selected from the group consisting of general arterial calcification of infancy (GACI), idiopathic infantile arterial calcification (IIAC), aging related hardening of arteries, progeria, pseudoxanthoma elasticum (PXE), medial wall vascular calcification (MWVC), end state renal disease (ESRD), chronic kidney disease-bone/mineral disorder (CKD-MBD), and calcific uremic arteriolopathy (CUA).

11. A method of treating pathological ossification in a subject in need thereof, the method comprising administering to the subject a therapeutically effective amount of a polypeptide comprising a soluble ecto-nucleotide pyrophosphate/phosphodiesterase-3 (ENPP3) polypeptide, whereby pathological ossification in the subject is treated.

12. The method of claim 11, wherein the pathological ossification is present in a disease selected from the group consisting of ossification of posterior longitudinal ligament (OPLL), autosomal recessive hypophosphatemia rickets type-2 (ARHR2), X-linked hypophosphatemia (XLH), age related osteopenia, and hypophosphatemic rickets.

13. The method of claim 11, wherein the soluble ENPP3 polypeptide comprises a C-terminal domain selected from the group consisting of a human IgG Fc domain and human serum albumin.

* * * * *

SEQUENCE LISTING

```
Sequence total quantity: 29
SEQ ID NO: 1           moltype = AA  length = 827
FEATURE                Location/Qualifiers
source                 1..827
                       mol_type = protein
                       organism = synthetic construct
SEQUENCE: 1
EKQGSCRKKC FDASFRGLEN CRCDVACKDR GDCCWDFEDT CVESTRIWMC NKFRCGETRL   60
```

```
EASLCSCSDD CLQRKDCCAD YKSVCQGETS WLEENCDTAQ QSQCPEGFDL PPVILFSMDG   120
FRAEYLYTWD TLMPNINKLK TCGIHSKYMR AMYPTKTFPN HYTIVTGLYP ESHGIIDNNM   180
YDVNLNKNFS LSSKEQNNPA WWHGQPMWLT AMYQGLKAAT YFWPGSEVAI NGSFPSIYMP   240
YNGSVPFEER ISTLLKWLDL PKAERPRFYT MYFEEPDSSG HAGGPVSARV IKALQVVDHA   300
FGMLMEGLKQ RNLHNCVNII LLADHGMDQT YCNKMEYMTD YFPRINFFYM YEGPAPRIRA   360
HNIPHDFFSF NSEEIVRNLS CRKPDQHFKP YLTPDLPKRL HYAKNVRIDK VHLFVDQQWL   420
AVRSKSNTNC GGGNHGYNNE FRSMEAIFLA HGPSFKEKTE VEPFENIEVY NLMCDLLRIQ   480
PAPNNGTHGS LNHLLKVPFY EPSHAEEVSK FSVCGFANPL PTESLDCFCP HLQNSTQLEQ   540
VNQMLNLTQE EITATVKVNL PFGRPRVLQK NVDHCLLYHR EYVSGFGKAM RMPMWSSYTV   600
PQLGDTSPLP PTVPDCLRAD VRVPPSESQK CSFYLADKNI THGFLYPPAS NRTSDSQYDA   660
LITSNLVPMY EEFRKMWDYF HSVLLIKHAT ERNGVNVVSG PIFDYNYDGH FDAPDEITKH   720
LANTDVPIPT HYFVVLTSCK NKSHTPENCP GWLDVLPFII PHRPTNVESC PEGKPEALWV   780
EERFTAHIAR VRDVELLTGL DFYQDKVQPV SEILQLKTYL PTFETTI                827

SEQ ID NO: 2            moltype = AA   length = 20
FEATURE                 Location/Qualifiers
source                  1..20
                        mol_type = protein
                        organism = synthetic construct
SEQUENCE: 2
MRGPAVLLTV ALATLLAPGA                                               20

SEQ ID NO: 3            moltype = AA   length = 22
FEATURE                 Location/Qualifiers
source                  1..22
                        mol_type = protein
                        organism = synthetic construct
SEQUENCE: 3
MRGPAVLLTV ALATLLAPGA GA                                            22

SEQ ID NO: 4            moltype = AA   length = 22
FEATURE                 Location/Qualifiers
source                  1..22
                        mol_type = protein
                        organism = synthetic construct
SEQUENCE: 4
MTSKFLLVSF ILAALSLSTT FS                                            22

SEQ ID NO: 5            moltype = AA   length = 95
FEATURE                 Location/Qualifiers
source                  1..95
                        mol_type = protein
                        organism = synthetic construct
SEQUENCE: 5
MERDGCAGGG SRGGEGGRAP REGPAGNGRD RGRSHAAEAP GDPQAAASLL APMDVGEEPL   60
EKAARARTAK DPNTYKIISL FTFAVGVNIC LGFTA                              95

SEQ ID NO: 6            moltype =     length =
SEQUENCE: 6
000

SEQ ID NO: 7            moltype =     length =
SEQUENCE: 7
000

SEQ ID NO: 8            moltype =     length =
SEQUENCE: 8
000

SEQ ID NO: 9            moltype =     length =
SEQUENCE: 9
000

SEQ ID NO: 10           moltype =     length =
SEQUENCE: 10
000

SEQ ID NO: 11           moltype =     length =
SEQUENCE: 11
000

SEQ ID NO: 12           moltype = AA   length = 16
FEATURE                 Location/Qualifiers
source                  1..16
                        mol_type = protein
                        organism = synthetic construct
SEQUENCE: 12
DSSSEEKFLR RIGRFG                                                   16
```

```
SEQ ID NO: 13           moltype = AA  length = 12
FEATURE                 Location/Qualifiers
source                  1..12
                        mol_type = protein
                        organism = synthetic construct
SEQUENCE: 13
EEEEEEEPRG DT                                                              12

SEQ ID NO: 14           moltype = AA  length = 12
FEATURE                 Location/Qualifiers
source                  1..12
                        mol_type = protein
                        organism = synthetic construct
SEQUENCE: 14
APWHLSSQYS RT                                                              12

SEQ ID NO: 15           moltype = AA  length = 12
FEATURE                 Location/Qualifiers
source                  1..12
                        mol_type = protein
                        organism = synthetic construct
SEQUENCE: 15
STLPIPHEFS RE                                                              12

SEQ ID NO: 16           moltype = AA  length = 12
FEATURE                 Location/Qualifiers
source                  1..12
                        mol_type = protein
                        organism = synthetic construct
SEQUENCE: 16
VTKHLNQISQ SY                                                              12

SEQ ID NO: 17           moltype =     length =
SEQUENCE: 17
000

SEQ ID NO: 18           moltype =     length =
SEQUENCE: 18
000

SEQ ID NO: 19           moltype = AA  length = 1147
FEATURE                 Location/Qualifiers
source                  1..1147
                        mol_type = protein
                        organism = synthetic construct
SEQUENCE: 19
MERDGCAGGG SRGGEGGRAP REGPAGNGRD RGRSHAAEAP GDPQAAASLL APMDVGEEPL          60
EKAARARTAK DPNTYKIISL FTFAVGVNIC LGFTAKQGSC RKKCFDASFR GLENCRCDVA         120
CKDRGDCCWD FEDTCVESTR IWMCNKFRCG ERLEASLCSC SDDCLQRKDC CADYKSVCQG         180
ETSWLEENCD TAQQSQCPEG FDLPPVILFS MDGFRAEYLY TWDTLMPNIN KLKTCGIHSK         240
YMRAMYPTKT FPNHYTIVTG LYPESHGIID NNMYDVNLNK NFSLSSKEQN NPAWWHGQSL         300
WLTAMYQGLK AATYFWPGSE VAINGSFPSI YMPYNGSVPF EERISTLLKW LDLPKAERPR         360
FYTMYFEEPD SSGHAGGPVS ARVIKALQVV DHAFGMLMEG LKQRNLHNCV NIILLADHGM         420
DQTYCNKMEY MTDYFPRINF FYMYEGPAPR IRAHNIPHDF FSFNSEEIVR NLSCRKPDQH         480
FKPYLTPDLP KRLHYAKNVR IDKVHLFVDQ QWLAVRSKSN TNCGGGNHGY NNEFRSMEAI         540
FLAHGPSFKE KTEVEPFENI EVYNLMCDLL RIQPAPNNGT HGSLNHLLKV PFYEPSHAEE         600
VSKFSVCGFA NPLPTESLDC FCPHLQNSTQ LEQVNQMLNL TQEEITATVK VNLPFGRPRV         660
LQKNVDHCLL YHREYVSGFG KAMRMPMWSS YTVPQLGDTS PLPPTVPDCL RADVRVPPSE         720
SQKCSFYLAD KNITHGFLYP PASNRTSDSQ YDALITSNLV PMYEEFRKMW DYFHSVLLIK         780
HATERNGVNV VSGPIFDYNY DGHFDAPDEI TKHLANTDVP IPTHYFVVLT SCKNKSHTPE         840
NCPGWLDVLP FIIPHRPTNV ESCPEGKPEA LWVEERFTAH IARVRDVELL TGLDFYQDKV         900
QPVSEILQLK TYLPTFETTI DKTHTCPPCP APELLGGPSV FLFPPKPKDT LMISRTPEVT         960
CVVVDVSHED PEVKFNWYVD GVEVHNAKTK PREEQYNSTY RVVSVLTVLH QDWLNGKEYK        1020
CKVSNKALPA PIEKTISKAK GQPREPQVYT LPPSREEMTK NQVSLTCLVK GFYPSDIAVE        1080
WESNGQPENN YKTTPPVLDS DGSFFLYSKL TVDKSRWQQG NVFSCSVMHE ALHNHYTQKS        1140
LSLSPGK                                                                 1147

SEQ ID NO: 20           moltype = AA  length = 227
FEATURE                 Location/Qualifiers
source                  1..227
                        mol_type = protein
                        organism = synthetic construct
SEQUENCE: 20
DKTHTCPPCP APELLGGPSV FLFPPKPKDT LMISRTPEVT CVVVDVSHED PEVKFNWYVD          60
GVEVHNAKTK PREEQYNSTY RVVSVLTVLH QDWLNGKEYK CKVSNKALPA PIEKTISKAK         120
GQPREPQVYT LPPSREEMTK NQVSLTCLVK GFYPSDIAVE WESNGQPENN YKTTPPVLDS         180
DGSFFLYSKL TVDKSRWQQG NVFSCSVMHE ALHNHYTQKS LSLSPGK                      227

SEQ ID NO: 21           moltype = AA  length = 1072
```

```
FEATURE                 Location/Qualifiers
source                  1..1072
                        mol_type = protein
                        organism = synthetic construct
SEQUENCE: 21
MRGPAVLLTV ALATLLAPGA KQGSCRKKCF DASFRGLENC RCDVACKDRG DCCWDFEDTC    60
VESTRIWMCN KFRCGERLEA SLCSCSDDCL QRKDCCADYK SVCQGETSWL EENCDTAQQS   120
QCPEGFDLPP VILFSMDGFR AEYLYTWDTL MPNINKLKTC GIHSKYMRAM YPTKTFPNHY   180
TIVTGLYPES HGIIDNNMYD VNLNKNFSLS SKEQNNPAWW HGQPMWLTAM YQGLKAATYF   240
WPGSEVAING SFPSIYMPYN GSVPFEERIS TLLKWLDLPK AERPRFYTMY FEEPDSSGHA   300
GGPVSARVIK ALQVVDHAFG MLMEGLKQRN LHNCVNIILL ADHGMDQTYC NKMEYMTDYF   360
PRINFFYMYE GPAPRIRAHN IPHDFFSFNS EEIVRNLSCR KPDQHFKPYL TPDLPKRLHY   420
AKNVRIDKVH LFVDQQWLAV RSKSNTNCGG GNHGYNNEFR SMEAIFLAHG PSFKEKTEVE   480
PFENIEVYNL MCDLLRIQPA PNNGTHGSLN HLLKVPFYEP SHAEEVSKFS VCGFANPLPT   540
ESLDCFCPHL QNSTQLEQVN QMLNLTQEEI TATVKVNLPF GRPRVLQKNV DHCLLYHREY   600
VSGFGKAMRM PMWSSYTVPQ LGDTSPLPPT VPDCLRADVR VPPSESQKCS FYLADKNITH   660
GFLYPPASNR TSDSQYDALI TSNLVPMYEE FRKMWDYFHS VLLIKHATER NGVNVVSGPI   720
FDYNYDGHFD APDEITKHLA NTDVPIPTHY FVVLTSCKNK SHTPENCPGW LDVLPFIIPH   780
RPTNVESCPE GKPEALWVEE RFTAHIARVR DVELLTGLDF YQDKVQPVSE ILQLKTYLPT   840
FETTIDKTHT CPPCPAPELL GGPSVFLFPP KPKDTLMISR TPEVTCVVVD VSHEDPEVKF   900
NWYVDGVEVH NAKTKPREEQ YNSTYRVVSV LTVLHQDWLN GKEYKCKVSN KALPAPIEKT   960
ISKAKGQPRE PQVYTLPPSR EEMTKNQVSL TCLVKGFYPS DIAVEWESNG QPENNYKTTP  1020
PVLDSDGSFF LYSKLTVDKS RWQQGNVFSC SVMHEALHNH YTQKSLSLSP GK          1072

SEQ ID NO: 22           moltype = AA  length = 1074
FEATURE                 Location/Qualifiers
source                  1..1074
                        mol_type = protein
                        organism = synthetic construct
SEQUENCE: 22
MTSKFLLVSF ILAALSLSTT FSKQGSCRKK CFDASFRGLE NCRCDVACKD RGDCCWDFED    60
TCVESTRIWM CNKFRCGERL EASLCSCSDD CLQRKDCCAD YKSVCQGETS WLEENCDTAQ   120
QSQCPEGFDL PPVILFSMDG FRAEYLYTWD TLMPNINKLK TCGIHSKYMR AMYPTKTFPN   180
HYTIVTGLYP ESHGIIDNNM YDVNLNKNFS LSSKEQNNPA WWHGQPMWLT AMYQGLKAAT   240
YFWPGSEVAI NGSFPSIYMP YNGSVPFEER ISTLLKWLDL PKAERPRFYT MYFEEPDSSG   300
HAGGPVSARV IKALQVVDHA FGMLMEGLKQ RNLHNCVNII LLADHGMDQT YCNKMEYMTD   360
YFPRINFFYM YEGPAPRIRA HNIPHDFFSF NSEEIVRNLS CRKPDQHFKP YLTPDLPKRL   420
HYAKNVRIDK VHLFVDQQWL AVRSKSNTNC GGGNHGYNNE FRSMEAIFLA HGPSFKEKTE   480
VEPFENIEVY NLMCDLLRIQ PAPNNGTHGS LNHLLKVPFY EPSHAEEVSK FSVCGFANPL   540
PTESLDCFCP HLQNSTQLEQ VNQMLNLTQE EITATVKVNL PFGRPRVLQK NVDHCLLYHR   600
EYVSGFGKAM RMPMWSSYTV PQLGDTSPLP PTVPDCLRAD VRVPPSESQK CSFYLADKNI   660
THGFLYPPAS NRTSDSQYDA LITSNLVPMY EEFRKMWDYF HSVLLIKHAT ERNGVNVVSG   720
PIFDYNYDGH FDAPDEITKH LANTDVPIPT HYFVVLTSCK NKSHTPENCP GWLDVLPFII   780
PHRPTNVESC PEGKPEALWV EERFTAHIAR VRDVELLTGL DFYQDKVQPV SEILQLKTYL   840
PTFETTIDKT HTCPPCPAPE LLGGPSVFLF PPKPKDTLMI SRTPEVTCVV VDVSHEDPEV   900
KFNWYVDGVE VHNAKTKPRE EQYNSTYRVV SVLTVLHQDW LNGKEYKCKV SNKALPAPIE   960
KTISKAKGQP REPQVYTLPP SREEMTKNQV SLTCLVKGFY PSDIAVEWES NGQPENNYKT  1020
TPPVLDSDGS FFLYSKLTVD KSRWQQGNVF SCSVMHEALH NHYTQKSLSL SPGK        1074

SEQ ID NO: 23           moltype = AA  length = 623
FEATURE                 Location/Qualifiers
source                  1..623
                        mol_type = protein
                        organism = synthetic construct
SEQUENCE: 23
GGGGSGGGGS GGGGSMKWVT FLLLLFVSGS AFSRGVFRRE AHKSEIAHRY NDLGEQHFKG    60
LVLIAFSQYL QKCSYDEHAK LVQEVTDFAK TCVADESAAN CDKSLHTLFG DKLCAIPNLR   120
ENYGELADCC TKQEPERNEC FLQHKDDNPS LPPFERPEAE AMCTSFKENP TTFMGHYLHE   180
VARRHPYFYA PELLYYAEQY NEILTQCCAE ADKESCLTPK LDGVKEKALV SSVRQRMKCS   240
SMQKFGERAF KAWAVARLSQ TFPNADFAEI TKLATDLTKV NKECCHGDLL ECADDRAELA   300
KYMCENQATI SSKLQTCCDK PLLKKAHCLS EVEHDTMPAD LPAIAADFVE DQEVCKNYAE   360
AKDVFLGTFL YEYSRRHPDY SVSLLLRLAK KYEATLEKCC AEANPPACYG TVLAEFQPLV   420
EEPKNLVKTN CDLYEKLGEY GFQNAILVRY TQKAPQVSTP TLVEAARNLG RVGTKCCTLS   480
EDQRLPCVED YLSAILNRVC LLHEKTPVSE HVTKCCSGSL VERRPCFSAL TVDETYVPKE   540
FKAETFTFHS DICTLPEKEK QIKKQTALAE LVKHKPKATA EQLKTVMDDF AQFLDTCCKA   600
ADKDTCFSTE GPNLVTRCKD ALA                                           623

SEQ ID NO: 24           moltype = AA  length = 1542
FEATURE                 Location/Qualifiers
source                  1..1542
                        mol_type = protein
                        organism = synthetic construct
SEQUENCE: 24
MERDGCAGGG SRGGEGGRAP REGPAGNGRD RGRSHAAEAP GDPQAAASLL APMDVGEEPL    60
EKAARARTAK DPNTYKIISL FTFAVGVNIC LGFTAKQGSC RKKCFDASFR GLENCRCDVA   120
CKDRGDCCWD FEDTCVESTR IWMCNKFRCG ERLEASLCSC SDDCLQRKDC CADYKSVCQG   180
ETSWLEENCD TAQQSQCPEG FDLPPVILFS MDGFRAEYLY TWDTLMPNIN KLKTCGIHSK   240
YMRAMYPTKT FPNHYTIVTG LYPESHGIID NNMYDVNLNK NFSLSSKEQN NPAWWHGQPM   300
WLTAMYQGLK AATYFWPGSE VAINGSFPSI YMPYNGSVPF EERISTLLKW LDLPKAERPR   360
```

```
FYTMYFEEPD SSSGHAGGPVS ARVIKALQVV DHAFGMLMEG LKQRNLHCNV NIIILLADHGM  420
DQTYCNKMEY MTDYFPRINF FYMYEGPAPR IRAHNIPHDF FSFNSEEIVR NLSCRKPDQH  480
FKPYLTPDLP KRLHYAKNVR IDKVHLFVDQ QWLAVRSKSN TNCGGGNHGY NNEFRSMEAI  540
FLAHGPSFKE KTEVEPFENI EVYNLMCDLL RIQPAPNNGT HGSLNHLLKV PFYEPSHAEE  600
VSKFSVCGFA NPLPTESLDC FCPHLQNSTQ LEQVNQMLNL TQEEITATVK VNLPFGRPRV  660
LQKNVDHCLL YHREYVSGFG KAMRMPMWSS YTVPQLGDTS PLPPTVPDCL RADVRVPPSE  720
SQKCSFYLAD KNITHGFLYP PASNRTSDSQ YDALITSNLV PMYEEFRKMW DYFHSVLLIK  780
HATERNGVNV VSGPIFDYNY DGHFDAPDEI TKHLANTDVP IPTHYFVVLT SCKNKSHTPE  840
NCPGWLDVLP FIIPHRPTNV ESCPEGKPEA LWVEERFTAH IARVRDVELL TGLDFYQDKV  900
QPVSEILQLK TYLPTFETTI GGGSGGGGSG GGGSMKWVTF LLLLFVSGSA FSRGVFRREA  960
HKSEIAHRYN DLGEQHFKGL VLIAFSQYLQ KCSYDEHAKL VQEVTDFAKT CVADESAANC  1020
DKSLHTLFGD KLCAIPNLRE NYGELADCCT KQEPERNECF LQHKDDNPSL PPFERPEAEA  1080
MCTSFKENPT TFMGHYLHEV ARRHPYFYAP ELLYYAEQYN EILTQCCAEA DKESCLTPKL  1140
DGVKEKALVS SVRQRMKCSS MQKFGERAFK AWAVARLSQT FPNADFAEIT KLATDLTKVN  1200
KECCHGDLLE CADDRAELAK YMCENQATIS SKLQTCCDKP LLKKAHCLSE VEHDTMPADL  1260
PAIAADFVED QEVCKNYAEA KDVFLGTFLY EYSRRHPDYS VSLLLRLAKK YEATLEKCCA  1320
EANPPACYGT VLAEFQPLVE EPKNLVKTNC DLYEKLGEYG FQNAILVRYT QKAPQVSTPT  1380
LVEAARNLGR VGTKCCTLPE DQRLPCVEDY LSAILNRVCL LHEKTPVSEH VTKCCSGSLV  1440
ERRPCFSALT VDETYVPKEF KAETFTFHSD ICTLPEKEKQ IKKQTALAEL VKHKPKATAE  1500
QLKTVMDDFA QFLDTCCKAA DKDTCFSTEG PNLVTRCKDA LA                     1542

SEQ ID NO: 25            moltype = AA  length = 1467
FEATURE                  Location/Qualifiers
source                   1..1467
                         mol_type = protein
                         organism = synthetic construct
SEQUENCE: 25
MRGPAVLLTV ALATLLAPGA KQGSCRKKCF DASFRGLENC RCDVACKDRG DCCWDFEDTC  60
VESTRIWMCN KFRCGERLEA SLCSCSDDCL QRKDCCADYK SVCQGETSWL EENCDTAQQS  120
QCPEGFDLPP VILFSMDGFR AEYLYTWDTL MPNINKLKTC GIHSKYMRAM YPTKTFPNHY  180
TIVTGLYPES HGIIDNNMYD VNLNKNFSLS SKEQNNPAWW HGQPMWLTAM YQGLKAATYF  240
WPGSEVAING SFPSIYMPYN GSVPFEERIS TLLKWLDLPK AERPRFYTMY FEEPDSSGHA  300
GGPVSARVIK ALQVVDHAFG MLMEGLKQRN LHCVNIIIL ADHGMDQTYC NKMEYMTDYF  360
PRINFFYMYE GPAPRIRAHN IPHDFFSFNS EEIVRNLSCR KPDQHFKPYL TPDLPKRLHY  420
AKNVRIDKVH LFVDQQWLAV RSKSNTNCGG GNHGYNNEFR SMEAIFLAHG PSFKEKTEVE  480
PFENIEVYNL MCDLLRIQPA PNNGTHGSLN HLLKVPFYEP SHAEEVSKFS VCGFANPLPT  540
ESLDCFCPHL QNSTQLEQVN QMLNLTQEEI TATVKVNLPF GRPRVLQKNV DHCLLYHREY  600
VSGFGKAMRM PMWSSYTVPQ LGDTSPLPPT VPDCLRADVR VPPSESQKCS FYLADKNITH  660
GFLYPPASNR TSDSQYDALI TSNLVPMYEE FRKMWDYFHS VLLIKHATER NGVNVVSGPI  720
FDYNYDGHFD APDEITKHLA NTDVPIPTHY FVVLTSCKNK SHTPENCPGW LDVLPFIIPH  780
RPTNVESCPE GKPEALWVEE RFTAHIARVR DVELLTGLDF YQDKVQPVSE ILQLKTYLPT  840
FETTIGGGSG GGGSGGGGSM KWVTFLLLLF VSGSAFSRGV FRREAHKSEI AHRYNDLGEQ  900
HFKGLVLIAF SQYLQKCSYD EHAKLVQEVT DFAKTCVADE SAANCDKSLH TLFGDKLCAI  960
PNLRENYGEL ADCCTKQEPE RNECFLQHKD DNPSLPPFER PEAEAMCTSF KENPTTFMGH  1020
YLHEVARRHP YFYAPELLYY AEQYNEILTQ CCAEADKESC LTPKLDGVKE KALVSSVRQR  1080
MKCSSMQKFG ERAFKAWAVA RLSQTFPNAD FAEITKLATD LTKVNKECCH GDLLECADDR  1140
AELAKYMCEN QATISSKLQT CCDKPLLKKA HCLSEVEHDT MPADLPAIAA DFVEDQEVCK  1200
NYAEAKDVFL GTFLYEYSRR HPDYSVSLLL RLAKKYEATL EKCCAEANPP ACYGTVLAEF  1260
QPLVEEPKNL VKTNCDLYEK LGEYGFQNAI LVRYTQKAPQ VSTPTLVEAA RNLGRVGTKC  1320
CTLPEDQRLP CVEDYLSAIL NRVCLLHEKT PVSEHVTKCC SGSLVERRPC FSALTVDETY  1380
VPKEFKAETF TFHSDICTLP EKEKQIKKQT ALAELVKHKP KATAEQLKTV MDDFAQFLDT  1440
CCKAADKDTC FSTEGPNLVT RCKDALA                                      1467

SEQ ID NO: 26            moltype = AA  length = 1469
FEATURE                  Location/Qualifiers
source                   1..1469
                         mol_type = protein
                         organism = synthetic construct
SEQUENCE: 26
MTSKFLLVSF ILAALSLSTT FSKQGSCRKK CFDASFRGLE NCRCDVACKD RGDCCWDFED  60
TCVESTRIWM CNKFRCGERL EASLCSCSDD CLQRKDCCAD YKSVCQGETS WLEENCDTAQ  120
QSQCPEGFDL PPVILFSMDG FRAEYLYTWD TLMPNINKLK TCGIHSKYMR AMYPTKTFPN  180
HYTIVTGLYP ESHGIIDNNM YDVNLNKNFS LSSKEQNNPA WWHGQPMWLT AMYQGLKAAT  240
YFWPGSEVAI NGSFPSIYMP YNGSVPFEER ISTLLKWLDL PKAERPRFYT MYFEEPDSSG  300
HAGGPVSARV IKALQVVDHA FGMLMEGLKQ RNLHCVNIIL LADHGMDQT YCNKMEYMTD  360
YFPRINFFYM YEGPAPRIRA HNIPHDFFSF NSEEIVRNLS CRKPDQHFKP YLTPDLPKRL  420
HYAKNVRIDK VHLFVDQQWL AVRSKSNTNC GGGNHGYNNE FRSMEAIFLA HGPSFKEKTE  480
VEPFENIEVY NLMCDLLRIQ PAPNNGTHGS LNHLLKVPFY EPSHAEEVSK FSVCGFANPL  540
PTESLDCFCP HLQNSTQLEQ VNQMLNLTQE EITATVKVNL PFGRPRVLQK NVDHCLLYHR  600
EYVSGFGKAM RMPMWSSYTV PQLGDTSPLP PTVPDCLRAD VRVPPSESQK CSFYLADKNI  660
THGFLYPPAS NRTSDSQYDA LITSNLVPMY EEFRKMWDYF HSVLLIKHAT ERNGVNVVSG  720
PIFDYNYDGH FDAPDEITKH LANTDVPIPT HYFVVLTSCK NKSHTPENCP GWLDVLPFII  780
PHRPTNVESC PEGKPEALWV EERFTAHIAR VRDVELLTGL DFYQDKVQPV SEILQLKTYL  840
PTFETTIGGG SGGGGSGGGG SMKWVTFLLL LFVSGSAFSR GVFRREAHKS EIAHRYNDLG  900
EQHFKGLVLI AFSQYLQKCS YDEHAKLVQE VTDFAKTCVA DESAANCDKS LHTLFGDKLC  960
AIPNLRENYG ELADCCTKQE PERNECFLQK DDNPSLPPF ERPEAEAMCT SFKENPTTFM  1020
GHYLHEVARR HPYFYAPELL YYAEQYNEIL TQCCAEADKE SCLTPKLDGV KEKALVSSVR  1080
QRMKCSSMQK FGERAFKAWA VARLSQTFPN ADFAEITKLA TDLTKVNKEC CHGDLLECAD  1140
DRAELAKYMC ENQATISSKL QTCCDKPLLK KAHCLSEVEH DTMPADLPAI AADFVEDQEV  1200
```

```
CKNYAEAKDV FLGTFLYEYS RRHPDYSVSL LLRLAKKYEA TLEKCCAEAN PPACYGTVLA    1260
EFQPLVEEPK NLVKTNCDLY EKLGEYGFQN AILVRYTQKA PQVSTPTLVE AARNLGRVGT    1320
KCCTLPEDQR LPCVEDYLSA ILNRVCLLHE KTPVSEHVTK CCSGSLVERR PCFSALTVDE    1380
TYVPKEFKAE TFTFHSDICT LPEKEKQIKK QTALAELVKH KPKATAEQLK TVMDDFAQFL    1440
DTCCKAADKD TCFSTEGPNL VTRCKDALA                                     1469

SEQ ID NO: 27           moltype = DNA   length = 3447
FEATURE                 Location/Qualifiers
source                  1..3447
                        mol_type = other DNA
                        organism = synthetic construct
SEQUENCE: 27
atggaaaggg acgatgcgc cggtggtgga tctcgcggag gcgaaggtgg aagggcccct    60
agggaaggac ctgccggaaa cggaagggac aggggacgct ctcacgccgc tgaagctcca    120
ggcgaccctc aggccgctgc ctctctgctg gctcctatgg acgtcggaga agaacccctg    180
gaaaaggccg ccagggccag gactgccaag gaccccaaca cctacaagat catctccctc    240
ttcactttcg ccgtcggagt caacatctgc ctgggattca ccgccgaaaa gcaaggcagc    300
tgcaggaaga agtgctttga tgcatcattt agaggactgg agaactgccg tgtgtgatgtg    360
gcatgtaaag accgaggtga ttgctgctgg gattttgaag acacctgtgt ggaatcaact    420
cgaatatgga tgtgcaataa atttcgttgt ggagagacca gattagaggc cagcctttgc    480
tcttgttcag atgactgttt gcagaggaaa gattgctgtg ctgactataa gagtgtttgc    540
caaggagaaa cctcatggct ggaagaaaac tgtgacacaa cccagcagtc tcagtgccca    600
gaagggtttg acctgccacc agttatcttg ttttctatgg atggatttag agctgaatat    660
ttatacacat gggatacttt aatgccaaat atcaataaac tgaaaacatg tggaattcat    720
tcaaaataca tgagagctat gtatcctacc aaaaccttcc caaatcatta ccattgtc      780
acgggcttgt atccagagtc acatggcatc attgacaata atatgttatga tgtaaatctc    840
aacaagaatt tttcactttc ttcaaaggaa caaataatc cagcctgttg gcatgggcaa    900
ccaatgtggc tgacagcaat gatcaaggtt taaaagccg ctacctactt ttggcccgga    960
tcagaagtgc ctataaatgg ctccttcct tccatataca tgcttacaa cggaagtgtc    1020
ccatttgaag agaggatttc tacactgta aaatggctga acctgcccaa agctgaaaga    1080
cccaggtttt ataccatgta ttttgaagaa cctgattcct ctggacatgc aggtggacca    1140
gtcagtgcca gagtaattaa agccttacag gtagtagatc atgcttttgg gatgttgatg    1200
gaaggcctga agcagcggaa tttgcacaac tgtgtcaata tcatccttct ggctgaccat    1260
ggaatggacc agacttattg taacaagatg gaatacatga ctgattattt tcccagaata    1320
aacttcttct acatgtacga aagggcctgcc ccccgcatcc gagctcataa tatacctcat    1380
gacttttta gttttaattc tgaggaaatt gttagaaacc tcagttgccg aaaacctgat    1440
cagcatttca agcccattt gactcctgat ttgccaaagc gactgcacta tgccaagaac    1500
gtcagaatcg acaaagttca tctctttgtg gatcaacagt ggctggctgt taggagtaaa    1560
tcaaatacaa attgtggagg aggcaaccat ggttataaca atgagttttag gagcatggag    1620
gctatctttc tggcacatgg acccagtttt aaagagaaga ctgaagttga accatttgaa    1680
aatattgaag tctataacct aatgtgtgat cttctacgca ttcaaccagc accaaacaat    1740
ggaacccatg gtagtttaaa ccatcttctg aaggtgcctt tttatgagcc atcccatgca    1800
gaggggtgt caaagttttc tgtttgtggc tttgctaatc cattgcccac agagtctctt    1860
gactgttttct gccctcacct acaaaatagt actcagctgg aacaagtgaa tcagatgcta    1920
aatctcaccc aagaagaaat aacagcaaca gtgaaagtaa atttgccatt tgggaggcct    1980
agggtactgc agaagaacgt ggaccactgt ctccttttacc acagggaata tgtcagtgga    2040
tttggaaaag ctatgaggat gcccatgtgg agttcatca cagtccccca gttgggagac    2100
acatcgcctc tgcctccac tgtcccagac tgtctgcggg ctgatgtcag ggttcctcct    2160
tctgagagcc aaaaatgttc cttctattta gcagacaaga atatcacccca ggcttcctc    2220
tatcctcctg ccagcaatag aacatcagat agccaatatg atgctttaat tactagcaat    2280
ttggtaccta tgtatgaaga attcagaaaa atgtgggact attccacag tgttcttctt    2340
ataaaacatg ccacagaaag aaatggagta atgtggttaa gtggaccaat atttgattat    2400
aattatgatg ccatttttga tgctccagat gaaattacca acatttagc caacactgat    2460
gttcccatcc aacacacta ctttgtggt ctgaccagtt gtaaaacaa gagccacaca    2520
ccggaaaact gccctgggtg gctggatgtc ctaccctta tcatccctca ccgacctacc    2580
aacgtggaga gctgtcctga aggtaaacca gaagctcttt gggttgaaga aagatttaca    2640
gctcacattg cccgggtccg tgatgtgaaa cttctcactg gcttgactt ctatcaggat    2700
aaagtgcagc ctgtctctga aattttgcaa ctaaagacat atttaccaac atttgaaacc    2760
actattgaca aaactcacac atgcccaccg tgcccacctc ctgaactcct gggggaccg    2820
tcagtcttcc tcttccccc aaaacccaag gacaccctca tgatctcccg gacccctacc    2880
gtcacatgcg tggtggtgga cgtgagccac gaagaccctg aggtcaagtt caactggtac    2940
gtggacggcg tggaggtgca taatgccaag acaaagccgc gggaggagca gtacaacagc    3000
acgtaccgtg tggtcagcgt cctcaccgtc ctgcaccagg actggctgaa tggcaaggag    3060
tacaagtgca aggtctccaa caaagccctc cagcccccca tcgagaaaacc catctccaaa    3120
gccaaagggc agccccgaga accacaggtg tacaccctgc ccccatcccg ggaggagatg    3180
accaagaacc aggtcagcct gacctgcctg gtcaaaggct tctatcccag cgacatcgcc    3240
gtggagtggg agagcaatgg gcagccggag aacaactaca agaccacgcc tcccgtgctg    3300
gactccgacg gctccttctt cctctatagc aagctcaccg tggacaagag caggtggcag    3360
caggggaacg tcttctcatg ctccgtgatg catgaggctc tgcacaacca ctacacgcag    3420
aagagcctct ccctgtcccc gggtaaa                                       3447

SEQ ID NO: 28           moltype = DNA   length = 4638
FEATURE                 Location/Qualifiers
source                  1..4638
                        mol_type = other DNA
                        organism = synthetic construct
SEQUENCE: 28
atggaaaggg acgatgcgc cggtggtgga tctcgcggag gcgaaggtgg aagggcccct    60
agggaaggac ctgccggaaa cggaagggac aggggacgct ctcacgccgc tgaagctcca    120
```

```
ggcgaccctc aggccgctgc ctctctgctg gctcctatgg acgtcggaga agaaccectg   180
gaaaaggccg ccagggccag gactgccaag gaccccaaca cctacaagat catctccctc   240
ttcactttcg ccgtcggagt caacatctgc ctgggattca ccgccgaaaa gcaaggcagc   300
tgcaggaaga agtgctttga tgcatcattt agaggactgg agaactgccg gtgtgatgtg   360
gcatgtaaag accgaggtga ttgctgctgg gattttgaag acacctgtgt ggaatcaact   420
cgaatatgga tgtgcaataa atttcgttgt ggagagacca gattagaggc cagcctttgc   480
tcttgttcag atgactgttt gcagaggaaa gattgctgtg ctgactataa gagtgtttgc   540
caaggagaaa cctcatggct ggaagaaaac tgtgacacag cccagcagtc tcagtgccca   600
gaaggggtttg acctgccacc agttatcttg ttttctatgg atggatttag agctgaatat   660
ttatacacat gggatacttt aatgccaaat atcaataaac tgaaaacatg tggaattcat   720
tcaaaataca tgagagctat gtatcctacc aaaaccttcc caaatcatta ccattgtc    780
acgggcttgt atccagagtc acatggcatc attgacaata atatgtatga tgtaaatctc   840
aacaagaatt tttcactttc ttcaaaggaa caaaataact cagcctggtg gcatgggcaa   900
ccaatgtggc tgacagcaat gtatcaaggt ttaaaagccg ctacctactt ttggcccgga   960
tcagaagtgg ctataaatgg ctcctttcct tccatataca tgccttacaa cggaagtgtc  1020
ccatttgaag agaggattte tacactgtta aaatggctgg acctgcccaa agctgaaaga  1080
cccaggtttt ataccatgta ttttgaagaa cctgattcct ctggacatgc aggtggacca  1140
gtcagtgcca gagtaattaa agccttacag gtagtagatc atgcttttgg gatgttgatg  1200
gaaggcctga agcagcggaa tttgcacaac tgtgtcaata tcatccttct ggctgaccat  1260
ggaatggacc agacttattg taacaagatg gaatacatga ctgattattt tcccagaata  1320
aacttcttct acatgtacga aggcctgccc cccgcatcc gagctcataa tatacctcat  1380
gacttttta gttttaattc tgaggaaatt gttagaaacc tcagttgccg aaaacctgat  1440
cagcatttca agccctattt gactcctgat ttgccaaagc gactgcacta tgccaagaac  1500
gtcagaatcg acaaagttca tctctttgtg gatcaacagt ggctggctgt taggagtaaa  1560
tcaaatacaa attgtggagg aggcaaccat ggttataaca atgagtttag gagcatggag  1620
gctatctttc tggcacatgg acccagtttt aaagagaaga ctgaagttga accatttgaa  1680
aatattgaag tctataacct aatgtgtgat cttctacgca ttcaaccagc accaaacaat  1740
ggaaacccatg gtagtttaaa ccatcttctg aaggtgcctt tttatgagcc atcccatgca  1800
gaggaggtgt caaagttttc tgtttgtggc tttgctaatc cattgccac agagtctctt  1860
gactgtttct gccctcacct acaaaaatagt actcagctgg aacaagtgaa tcagatgcta  1920
aatctcaccc aagaagaaat aacagcaaca gtgaaagtaa atttgccatt gggaggcct   1980
agggtactgc agaagaacgt ggaccactgt ctcctttacc acaggggata tgtcagtgga  2040
tttgaaaaag ctatgaggat gcccatgtgg agttcataca cagtccccca gttgggagac  2100
acatcgcctc tgcctcccac tgtcccagac tgtctgcggg ctgatgtcag ggttcctcgt  2160
tctgagagcc aaaaatgttc cttctattta gcagacaaga atatcaccca cggcttcctc  2220
tatcctcctg ccagcaatag aacatcagat agccaatatg atgctttaat tactagcaat  2280
ttggtaccta tgtatgaaga attcagaaaa atgtgggact acttccacag tgttcttctt  2340
ataaaacatg ccacagaaag aaatggagta aatgtggtta gtggaccaat atttgattat  2400
aattatgatg gccattttga tgctccagat gaaattacca aacatttagc caacactgat  2460
gttcccatcc caacacactga ctttgtggtg ctgaccagtt gtaaaaacaa gagccacaca  2520
ccggaaaact gccctgggtg gctggatgtc ctacccttta tcatccctca ccgacctacc  2580
aacgtggaga gctgtcctga aggtaaacca gaagctcttt gggttgaaga aagattttaca  2640
gctcacattg cccgggtccg tgatgtagaa cttctcactg ggcttgactt ctatccaggat  2700
aaagtgcagc ctgtctctga aattttgcaa ctaaagacat attttaccaac atttgaaacc  2760
actattggtg gaggagctc tggtggaggc ggtagcggag gcggagggtc gatgaagtgg  2820
gtaacctttta tttcccttct ttttctcttt agctcggctt attccagggg tgtgtttcgt  2880
cgagatgcac acaagatgga ggtgctcat cggtttaaaa atttgggaga gaaaatttc  2940
aaagccttgg tgttgattgc ctttgctcag tatcttcagc agtgtccatt tgaagatcat  3000
gtaaaattag tgaatgaagt aactgaattt gcaaaaacat gtgttgctga tgagtcagct  3060
gaaaatttgtg acaaatcact tcatacccttt tttggagaca attatgcac agttgcaact  3120
cttcgtgaaa cctatggtga aatgctgtga aacaagaacc tgagagaaat  3180
gaatgcttct tgcaacacaa agatgacaac ccaaacctcc cccgattggt gagaccagag  3240
gttgatgtga tgtgcactgc ttttcatgac aatgaagaga ctttttgaa aaaatactta  3300
tatgaaattg ccagaagaca tccttacttt tatgcccegg aactccttt ctttgctaaa  3360
aggtataaag ctgctttttac agaatgttgc aagctgtca ataaagctgc ctgcctgttg  3420
ccaaagctcg atgaacttcg ggatgaaggg aaggcttcgt ctgccaaaca gagactcaag  3480
tgtgccagtc tccaaaaatt tggagaaaga gctttcaaag catgggcagt agctcgcctg  3540
agccagagat ttcccaaagc tgagtttgca gaagtttcca gttagtgac agatcttacc  3600
aaagtccaca cggaatgctg ccatggagat ctgcttgaat gtgctgatga cagggcgac  3660
cttgccaagt atatctgtga aaatcaagat tcgatctcca gtaaactgaa ggaatgctgt  3720
gaaaaacctc tgttggaaaa atcccactgc attgccgaag tggaaaatga tgagatgcct  3780
gctgacttgc cttcattagc tgctgatttt gttgaaagta aggatgtttg caaaaactat  3840
gctgaggcaa aggatgtctt cctgggcatg ttttttgtatg aatatgcaag aaggcatcct  3900
gattactctg tcgtgctgct gctgagactt gccaagacat atgaaaccac tctagaagag  3960
tgctgtgccg ctgcagatcc tcatgaatgc tatgccaaag tgttcgatga atttaaacct  4020
cttgtggaag agcctcagaa tttaatcaaa caaaattgtg agcttttga gcagcttgga  4080
gagtacaaat tccagaatgc gctattagtt cgttacacca gaaagtaccc caagtgtca   4140
actccaactc ttgtagaggt ctcaagaaac ctaggaaatg tgggcagcaa atgttgtaaa  4200
catcctgaag caaaagaat gccctgtgca gaagactatc tatccgtggt cctgaaccag  4260
ttatgtgtgt tgcatgagaa aacgccagta agtgacagag tcaccaaatg ctgcacagaa  4320
tccttggtga acaggcgacc atgctttca gctctggaag tcgatgaaac atacgttccc  4380
aaagagttta atgctgaaac attcaccttc catgcagata tatgcacact ttctgagaag  4440
gagagacaaa tcaagaaaca aactgcactt gttgagctct gaaacacaa gcccaaggca  4500
acaaaagagc aactgaaagc tgtttatgat gatttcgcag cttttgtaga gaagtgctgc  4560
aaggctgacg ataaggagac ctgcttttgcc gaggagggta aaaaacttgt tgctgcaagt  4620
caagctgcct taggctta                                                  4638
SEQ ID NO: 29    moltype = DNA  length = 8852
FEATURE          Location/Qualifiers
```

```
source                  1..8852
                        mol_type = other DNA
                        organism = synthetic construct
SEQUENCE: 29
gacggatcgg gagatctccc gatcccctat ggtcgactct cagtacaatc tgctctgatg   60
ccgcatagtt aagccagtat ctgctccctg cttgtgtgtt ggaggtcgct gagtagtgcg  120
cgagcaaaat ttaagctaca acaaggcaag cttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggac tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gcttatggaa  900
agggacggat gcgccggtgg tggatctcgc ggaggcgaag gtggaagggc ccctaggaa  960
ggacctgccg gaaacggaag ggacagggga cgctctcacg ccgctgaagc tccaggcgac 1020
cctcaggccg ctgcctctct gctgctcctg atggacggga gcgaagaaacc cctggaaaag 1080
gccgccaggg ccaggactgc caaggacccc aacacctaca agatcatctc cctcttcact 1140
ttcgccgtcg gagtcaacat ctgcctggga ttcaccgccg aaaagcaagg cagctgcagg 1200
aagaagtgct tgatgcatc atttagagga ctggagaact gccggtgtga tgtggcatgt 1260
aaagaccgag gtgattgctg ctgggatttt gaagcaacgc gtgtgaatc aactcgaata 1320
tggatgtgca ataaatttcg ttgtggagag accagattag aggccagcct ttgctcttgt 1380
tcagatgact gtttgcagag gaaagattgc tgtgctgact ataagagtgt ttgccaagga 1440
gaaacctcat ggctggaaga aaactgtgac acagcccagc agtctcagtg cccagaaggg 1500
tttgacctgc caccagttat ctttgttttct atggatggat ttagagctga atattatac 1560
acatgggata cttttaatgcc aaatatcaat aaactgaaaa catgtggaat tcattcaaaa 1620
tacatgagag ctatgtatcc taccaaaacc ttcccaaatc attacaccat tgtcacgggc 1680
ttgtatccag agtcacatgg catcattgac aataatatgt atgatgtaaa tctcaacaag 1740
aattttttcac tttcttcaaa ggaacaaaat aatccagtcc ggtggctgg gcaaccaatg 1800
tggctgacag caatgtatca aggttttaaaa gccgctacct acttttggcc cggatcagaa 1860
gtggctataa atggctcctt tccttccata tacatgcctt acaacggaag tgtcccattt 1920
gaagagagga tttctacact gttaaaatgg ctggacctgc ccaaagctga aagacccagg 1980
ttttatacca tgtattttga agaacctgat tcctctggac atgcaggtgg accagtcagt 2040
gccagagtaa ttaaagcctt acaggtagta gatcatgctt tgggatgtt gatggaaggc 2100
ctgaagcagc ggaatttgca caactgtgtc aatatcatcc ttctggctga ccatggaatg 2160
gaccagactt attgtaacaa gatggaatac atgactgatt attttcccag aataaacttc 2220
ttctacatgt acgaagggcc tgccccccgc atccgagctc ataatatacc tcatgacttt 2280
tttagtttta attctgagga aattgttaga aactcagtt gccgaaaacc tgatcagcat 2340
ttcaagccct atttgactcc tgatttgcca aagcgactgc actatgccaa gaacgtcaga 2400
atcgacaaag ttcatctctt tgtggatcaa cagtggctgg ctgttaggag taaatcaaat 2460
acaaattgtg gaggaggcaa ccatggttat aacaatgagt ttaggagcat ggaggctatc 2520
tttctggcac atgacccag ttttaaagag aagactaagt ttgaaccatt tgaaaatatt 2580
gaagtctata acctaatgtg tgatcttcta cgcattcaac cagcaccaaa caatggaacc 2640
catggtagtt taaccatct tctgaaggtg cctttttatg agccatccca tgcagaggag 2700
gtgtcaaagt tttctgtttg tggctttgct aatccattgc ccacagagtc tcttgactgt 2760
ttctgccctc acctacaaaa tagtactcag ctggaacaag tgaatcagat gctaaatcct 2820
acccaagaag aaataacagc aacagtgaaa gtaaatttgc catttgggag gcctagggta 2880
ctgcagaaga acgtggacca ctgtctcctt taccacaggg aatatgtcag tggatttgga 2940
aaagctatga ggatgcccat gtggagttca tacacagtcc cccagttggg agacacatcg 3000
cctctgcctc ccactgtccc agactgtctg cgggctgatg tcagggttcc tccttctgag 3060
agccaaaaat gttccttcta tttagcagac aagaatatca cccacggctt cctctatcct 3120
cctgccagca atagaacatc agatagccaa tatgatgctt taattactag caatttggta 3180
cctatgtatg aagaattcag aaaaatgtgg gactacttcc acagtgttct tcttataaaa 3240
catgccacag aaagaaatgg agtaaatgtg gttagtggac caatatttga ttataattat 3300
gatggccatt ttgatgctcc agatgaaatt accaaacatt tagccaacac tgatgttccc 3360
atcccaacac actactttgt ggtgctgacc agttgtaaaa acaagagcca cacaccggaa 3420
aactgccctg ggtggctgga tgtcctaccc tttatcatcc ctcaccgacc taccaacgtg 3480
gagagctgtc ctgaaggtaa accagaagct ctttgggttg aagaaagatt tacagctcac 3540
attgcccggg tccgtgatgt agaacttctc actgggcttg acttctatca ggataaagtg 3600
cagcctgtct ctgaaatttt gcaactaaag acatattac caacatttga aaccactatt 3660
gacaaaactc acacatgccc accgtgccca gcacctgaac tcctgggggg accgtcagtc 3720
ttcctcttcc ccccaaaacc caaggacacc ctcatgatct cccggacccc tgaggtcaca 3780
tgcgtggtgg tggacgtgag ccacgaagac cctgaggtca agttcaactg gtacgtggac 3840
ggcgtggagg tgcataatgc caagacaaag ccgcgggagg agcagtacaa cagcacgtac 3900
cgtgtggtca gcgtcctcac cgtcctgcac caggactggc tgaatggcaa ggagtacaag 3960
tgcaaggtct ccaacaaagc cctcccagcc cccatcgaga aaccatctc caaagccaaa 4020
gggcagcccc gagaaccaca ggtgtacacc ctgcccccat cccgggagga gatgaccaag 4080
aaccaggtca gcctgacctg cctggtcaaa ggcttctatc cagcgacat cgccgtggag 4140
tgggagagca atgggcagcc ggagaacaac tacaagacca cgcctcccgt gctggactcc 4200
gacggctcct tcttcctcta tagcaagctc accgtggaca agagcaggtg gcagcagggg 4260
aacgtcttct catgctccgt gatgcatgag gctctgcaca accactacac gcagaagagc 4320
ctctccctgt cccggggtaa atgaaattct gcagatatcc atcacactgg cggccgctcg 4380
agcatgcatc tagagggccc tattctatag tgtcacctaa atgctagagc tcgctgatca 4440
gcctcgactg tgccttctag ttgccagcca tctgttgttt gcccctcccc cgtgccttcc 4500
```

```
ttgaccctgg aaggtgccac tcccactgtc ctttcctaat aaaatgagga aattgcatcg   4560
cattgtctga gtaggtgtca ttctattctg gggggtgggg tggggcagga cagcaagggg   4620
gaggattggg aagacaatag caggcatgct ggggatgcgg tgggctctat ggcttctgag   4680
gcggaaagaa ccagctgggg ctctaggggg tatccccacg cgccctgtag cggcgcatta   4740
agcgcggcg gtgtggtggt tacgcgcagc gtgaccgcta cacttgccag cgccctagcg   4800
cccgctcctt tcgctttctt cccttccttt ctcgccacgt tcgccggctt tccccgtcaa   4860
gctctaaatc ggggcatccc tttagggttc cgatttagtg ctttacggca cctcgacccc   4920
aaaaaacttg attagggtga tggttcacgt agtgggccat cgccctgata dacggttttt   4980
cgcccttga cgttggagtc cacgttcttt aatagtggac tcttgttcca aactggaaca   5040
acactcaacc ctatctcggt ctattctttt gatttataag ggattttggg gatttcggcc   5100
tattggttaa aaaatgagct gatttaacaa aaatttaacg cgaattaatt ctgtggaatg   5160
tgtgtcagtt agggtgtgga aagtcccag gctccccagg caggcagaag tatgcaaagc   5220
atgcatctca attagtcagc aaccaggtgt ggaaagtccc caggctcccc agcaggcaga   5280
agtatgcaaa gcatgcatct caattagtca gcaaccatag tcccgcccct aactccgccc   5340
atcccgcccc taactccgcc cagttccgcc cattctccgc cccatggctg actaattttt   5400
tttatttatg cagaggccga ggccgcctct gcctctgagc tattccagaa gtagtgagga   5460
ggcttttttg gaggcctagg ctttttgcaaa aagctcccgg gagcttgtat atccatttc   5520
ggatctgatc aagagacagg atgaggatcg tttcgcatga ttgaacaaga tggattgcac   5580
gcaggttctc cggccgcttg ggtggagagg ctattcggct atgactgggc acaacagaca   5640
atcggctgct ctgatgccgc cgtgttccgg ctgtcagcgc aggggcgccc ggttcttttt   5700
gtcaagaccg acctgtccgg tgccctgaat gaactgcagg acgaggcagc gcggctatcg   5760
tggctggcca cgacgggcgt tccttgcgca gctgtgctcg acgttgtcac tgaagcggga   5820
agggactggc tgctattggg cgaagtgccg gggcaggatc tcctgtcatc tcaccttgct   5880
cctgccgaga aagtatccat catggctgat gcaatgcggc ggctgcatac gcttgatccg   5940
gctacctgcc cattcgacca ccaagcgaaa catcgcatcg agcgagcacg tactcggatg   6000
gaagccggtc ttgtcgatca ggatgatctg gacgaagagc atcaggggct cgcgccagcc   6060
gaactgttcg ccaggctcaa ggcgcgcatg cccgacggcg aggatctcgt cgtgacccat   6120
ggcgatgcct gcttgccgaa tatcatggtg gaaaatggcc gcttttctgg attcatcgac   6180
tgtggccggc tgggtgtggc ggaccgctat caggacatag cgttggctac ccgtgatatt   6240
gctgaagagc ttggcggcga atgggctgac cgcttcctcg tgctttacgg tatcgccgct   6300
cccgattcgc agcgcatcgc cttctatcgc cttcttgacg agttcttctg agcgggactc   6360
tggggttcga aatgaccgac caagcgacgc ccaacctgcc atcacgagat ttcgattcca   6420
ccgccgcctt ctatgaaagg ttgggcttcg gaatcgtttt ccgggacgcc ggctggatga   6480
tcctccagcg cggggatctc atgctggagt tcttcgccca ccccaacttg tttattgcag   6540
cttataatgg ttacaaataa agcaatagca tcacaaattt cacaaataaa gcatttttt   6600
cactgcattc tagttgtggt ttgtccaaac tcatcaatgt atcttatcat gtctgtatac   6660
cgtcgacctc tagctagagc ttggcgtaat catggtcata gctgtttcct gtgtgaaatt   6720
gttatccgct cacaattcca cacaacatac gagccggaag cataaagtgt aaagcctggg   6780
gtgcctaatg agtgagctaa ctcacattaa ttgcgttgcg ctcactgccc gctttccagt   6840
cgggaaacct gtcgtgccag ctgcattaat gaatcggcca acgcgcgggg agaggcggtt   6900
tgcgtattgg gcgctcttcc gcttcctcgc tcactgactc gctgcgctcg tcgttcggc   6960
tgcggcgagc ggtatcagct cactcaaagg cggtaatacg gttatccaca gaatcagggg   7020
ataacgcagg aaagaacatg tgagcaaaag gccagcaaaa ggccaggaac cgtaaaaagg   7080
ccgcgttgct ggcgtttttc cataggctcc gcccccctga cgagcatcac aaaaatcgac   7140
gctcaagtca gaggtggcga aacccgacag gactataaag ataccaggcg tttccccctg   7200
gaagctccct cgtgcgctct cctgttccga ccctgccgct taccggatac ctgtccgcct   7260
ttctcccttc gggaagcgtg gcgctttctc aatgctcacg ctgtaggtat ctcagttcgg   7320
tgtaggtcgt tcgctccaag ctgggctgtg tgcacgaacc cccgttcag cccgaccgct   7380
gcgccttatc cggtaactat cgtcttgagt ccaacccggt aagacacgac ttatcgccac   7440
tggcagcagc cactggtaac aggattagca gagcgaggta tgtaggcggt gctacagagt   7500
tcttgaagtg gtggcctaac tacggctaca ctagaaggac agtatttggt atctgcgctc   7560
tgctgaagcc agttaccttc ggaaaaagag ttggtagctc ttgatccggc aaacaaacca   7620
ccgctgtag cggtggtttt tttgtttgca agcagcagat tacgcgcaga aaaaaaggat   7680
ctcaagaaga tccttttgatc ttttctacgg gtctgacgc tcagtggaac gaaaactcac   7740
gttaagggat tttggtcatg agattatcaa aaaggatctt cacctagatc cttttaaatt   7800
aaaaatgaag ttttaaatca atctaaagta tatatgagta acttggtct gacagttacc   7860
aatgcttaat cagtgaggca cctatctcag cgatctgtct atttcgttca tccatagttg   7920
cctgactccc cgtcgtgtag ataactacga tacgggaggg cttaccatct ggccccagtg   7980
ctgcaatgat accgcgagac ccacctcac cggctccaga tttatcagca ataaaccagc   8040
cagccggaag ggccgagcgc agaagtggtc ctgcaacttt atccgcctcc atccagtcta   8100
ttaattgttg ccgggaagct agagtaagta gttcgccagt taatagtttg cgcaacgttg   8160
ttgccattgc tacaggcatc gtggtgtcac gctcgtcgtt tggtatggct tcattcagct   8220
ccggttccca acgatcaagg cgagttacat gatcccccat gttgtgcaaa aaagcggtta   8280
gctccttcgg tcctccgatc gttgtcagaa gtaagttggc cgcagtgtta tcactcatgg   8340
ttatggcagc actgcataat tctcttactg tcatgccatc cgtaagatgc ttttctgtga   8400
ctggtgagta ctcaaccaag tcattctgag aatagtgtat gcggcgaccg agttgctctt   8460
gcccggcgtc aatacgggat aataccgcgc cacatagcag aactttaaaa gtgctcatca   8520
ttggaaaacg ttcttcgggg cgaaaactct caaggatctt accgctgttg agatccagtt   8580
cgatgtaacc cactcgtgca cccaactgat cttcagcatc ttttactttc accagcgttt   8640
ctgggtgagc aaaaacagga aggcaaaatg ccgcaaaaaa gggaataagg gcgacacgga   8700
aatgttgaat actcatactc ttcctttttc aatattattg aagcatttat cagggttatt   8760
gtctcatgag cggatacata tttgaatgta tttagaaaaa taaacaaata ggggttccgc   8820
gcacatttcc ccgaaaagtg ccacctgacg tc                                 8852
```